(12) United States Patent
Minamiguchi et al.

(10) Patent No.: US 10,194,939 B2
(45) Date of Patent: Feb. 5, 2019

(54) SENSOR EMBEDDING DEVICE AND SENSOR EMBEDDING SYSTEM

(71) Applicant: PANASONIC INTELLECTUAL PROPERTY MANAGEMENT CO., LTD., Osaka (JP)

(72) Inventors: Masaru Minamiguchi, Kyoto (JP); Yasuaki Okumura, Kyoto (JP); Tatsurou Kawamura, Kyoto (JP); Takahiro Aoki, Hyogo (JP); Masahiko Shioi, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 598 days.

(21) Appl. No.: 14/941,007

(22) Filed: Nov. 13, 2015

(65) Prior Publication Data

US 2016/0066953 A1   Mar. 10, 2016

Related U.S. Application Data

(63) Continuation of application No. PCT/JP2014/002534, filed on May 14, 2014.

(30) Foreign Application Priority Data

May 17, 2013   (JP) .................. 2013-104708
May 17, 2013   (JP) .................. 2013-104709
May 17, 2013   (JP) .................. 2013-104710

(51) Int. Cl.
*A61B 5/00*        (2006.01)
*A61B 17/34*       (2006.01)
(Continued)

(52) U.S. Cl.
CPC ........ *A61B 17/3468* (2013.01); *A61B 5/1459* (2013.01); *A61B 5/14546* (2013.01);
(Continued)

(58) Field of Classification Search
CPC . A61B 5/14503; A61B 5/1459; A61B 5/1464; A61B 5/1473; A61B 5/1482; A61B 5/14865; A61B 5/14532; A61B 17/3468
See application file for complete search history.

(56) References Cited

U.S. PATENT DOCUMENTS 5,611,813 A * 3/1997 Lichtman ............ A61B 17/29
                                                    606/174
5,910,148 A * 6/1999 Reimels ............ A61B 17/0483
                                                    606/139
(Continued)

FOREIGN PATENT DOCUMENTS

JP      2009-273610 A     11/2009
JP      2010-000284 A      1/2010
(Continued)

OTHER PUBLICATIONS

Yuen, J.M. et al., "Transcutaneous Glucose Sensing by Surface-Enhanced Spatially Offset Raman Spectroscopy in a Rat Model", Letters to Analytical Chemistry, vol. 82. (2010), pp. 8382-8385.
(Continued)

*Primary Examiner* — Eric Winakur
*Assistant Examiner* — Chu Chuan (JJ) Liu
(74) *Attorney, Agent, or Firm* — McDermott Will & Emery LLP

(57) ABSTRACT

A sensor embedding device according to the present disclosure is a sensor embedding device which embeds a sensor in a subject, the sensor having a sensing region in which to detect a state of the subject, including: a needle to be inserted in the subject, the needle having a hole; a sensor retainer to retain the sensor so that the sensor is ready to be embedded inside the subject in such a manner that the sensing region is oriented in a predetermined direction; and a movable
(Continued)

section to move the sensor into the subject with a slide of the sensor retainer inside the hole.

24 Claims, 22 Drawing Sheets

(51) Int. Cl.
*A61B 5/1459* (2006.01)
*G01N 21/65* (2006.01)
*G01N 21/64* (2006.01)
*A61B 5/1455* (2006.01)
*A61B 5/145* (2006.01)

(52) U.S. Cl.
CPC .......... *A61B 5/14556* (2013.01); *A61B 5/686* (2013.01); *G01N 21/645* (2013.01); *G01N 21/65* (2013.01); *A61B 5/6849* (2013.01); *G01N 21/658* (2013.01); *G01N 2021/6417* (2013.01)

(56) References Cited

U.S. PATENT DOCUMENTS

2005/0221276 A1* 10/2005 Rozakis ................. C12Q 1/001
  435/4
2012/0029326 A1    2/2012  Kawamura et al.

FOREIGN PATENT DOCUMENTS

JP    2012-519833 A    8/2012
WO    02/30275 A1    4/2002
WO    03/072172 A2    9/2003

OTHER PUBLICATIONS

International Search Report dated Jul. 1, 2014, issued in corresponding International Application No. PCT/JP2014/002534. (w/ English translation).

* cited by examiner

SENSOR EMBEDDING DEVICE AND SENSOR EMBEDDING SYSTEM

This is a continuation of International Application No. PCT/JP2014/002534, with an international filing date of May 14, 2014, which claims priority of Japanese Patent Application Nos. 2013-104708, 2013-104709 and 2013-104710, all filed on May 17, 2013, the contents of which are hereby incorporated by reference.

BACKGROUND

1. Technical Field

The present application relates to a device with which to embed a sensor in a subject.

2. Description of the Related Art

There have been proposed methods which involve irradiating a biological body with light from outside of a biological body, and detecting reflected light or transmitted light therefrom/therethrough in order to measure the concentration of an analyte, e.g., glucose.

For example, microparticles that contain a reagent whose fluorescence property changes through reaction with glucose may be embedded as sensors in the upper layer of the skin, and the microparticle sensors may be irradiated with light from outside of the biological body in order to transdermally detect fluorescence occurring from the microparticle sensors. A method which measures glucose concentration in this manner is disclosed in International Publication No. 2002/030275.

Moreover, a method has been proposed in which a sensor having a sensing region on its surface is embedded in a biological body, and glucose concentration is monitored by utilizing surface-enhanced Raman spectroscopy or other surface-enhanced spectral sensitization techniques (J. M. Yuen, N. C. Shah et. al., Anal. Chem. (2010)82, 8382-8385).

In order to embody a method of embedding a sensor in the skin, an injection device has been proposed which elevates or depresses a part of the skin, and injects a substance to be injected at a predetermined position and depth (International Publication No. 2003/072172).

SUMMARY

The conventional techniques have a problem in that it is impossible to embed a sensor inside the subject in such a manner that its sensing region is oriented in a predetermined direction.

One non-limiting, and exemplary embodiment provides a sensor embedding device for embedding a sensor in a subject, the sensor having a sensing region in which to detect a state of the subject, comprising: a needle to be inserted in the subject, the needle having a hole; a sensor retainer to retain the sensor so that the sensor is ready to be embedded inside the subject in such a manner that the sensing region is oriented in a predetermined direction; and a movable section to move the sensor into the subject with a slide of the sensor retainer inside the hole.

According to the present disclosure, a sensor can be embedded inside a subject in such a manner that its sensing region is oriented in a predetermined direction.

These general and specific aspects may be implemented using a device, a system, and a method, and any combination of devices, systems, and methods.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

DETAILED DESCRIPTION

Figure 1:
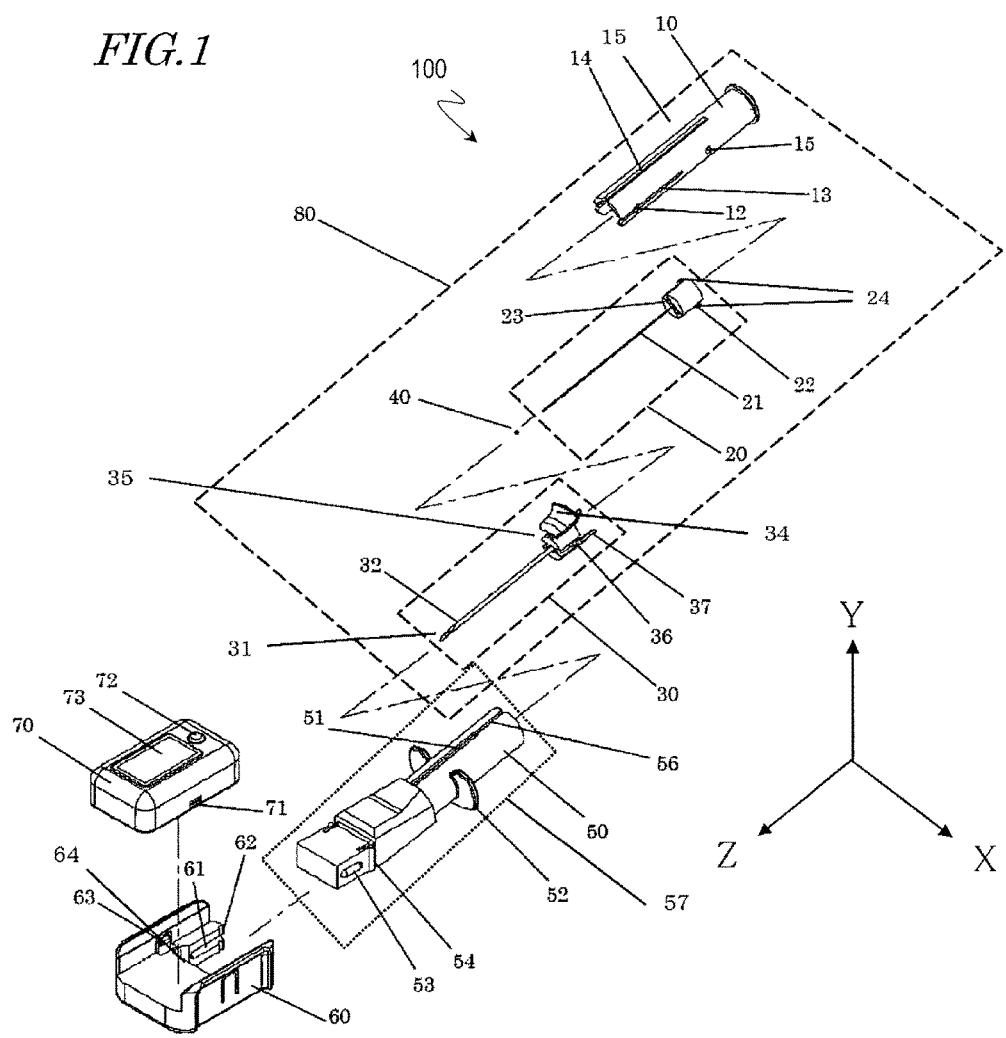
FIG. 1 is an exploded view showing an exemplary construction of a sensor embedding device 100 according to Embodiment 1 of the present disclosure.

Hereinafter, embodiments of the present disclosure will be described with reference to the drawings. First, a viewpoint of the inventors will be described.

When light is radiated from the surface of a subject (e.g., the skin surface of a biological body), and resultantly occurring light is to be detected from outside of the subject (e.g., transdermally detected), it would be advantageous to control the tilt of the sensor within the subject. In other words, when performing a detection from the skin surface of a biological body, for example, it would be advantageous to control the sensor surface so that its sensing region is oriented toward the skin surface.

The skin consists of epithelial tissue (having a thickness of about 0.2 to about 0.5 mm) at the biological surface and dermis tissue (having a thickness of about 0.5 to about 2 mm) underlying the epithelial tissue. Light which is radiated from outside of the biological body becomes diffused, scattered, or absorbed under the skin. Therefore, when a sensor is located at a deep site in the skin, the intensity of light which is radiated onto the sensor will be weak if its sensor surface having a sensing region is not oriented toward the skin surface. Furthermore, the light occurring from the sensor surface will also be weak. These will weaken the light intensity for transdermal detection.

Therefore, in order to optimize the sensitivity in detecting the state of a subject (e.g., glucose concentration measurement), it is necessary to place the sensor at a predetermined depth, and orient the sensor surface in a predetermined direction (e.g., toward the skin surface).

When an injection device as used in the conventional techniques is utilized in embedding a sensor, there is a possibility that the sensor may rotate within the injection needle. Therefore, the sensor cannot always be embedded in such a manner that its sensing region is oriented in a predetermined direction (e.g., toward the skin surface). Consequently, one cannot obtain sufficient sensitivity for detecting the subject state (e.g., glucose concentration measurement), for example.

Embodiments of the present invention that are based on the above-discussed viewpoint will be described below. First, an implementation of the present invention will be described in outline.

A sensor embedding device according to one implementation of the present invention is a sensor embedding device for embedding a sensor in a subject, the sensor having a sensing region for detecting a state of the subject. The sensor embedding device according to one implementation comprises a needle, a sensor retainer, and a movable section. The needle is to be inserted in the subject, the needle having a hole. The sensor retainer retains the sensor so that the sensor is ready to be embedded inside the subject in such a manner that the sensing region is oriented in a predetermined direction. The movable section moves the sensor into the subject with a slide of the sensor retainer inside the hole.

In one implementation, the sensor retainer includes a first grip portion and a second grip portion. The sensor may become retained as the sensor is sandwiched between the first grip portion and the second grip portion.

In one implementation, the sensor is released from retention when the sensor retainer goes outside the hole.

In one implementation, the distance between the first grip portion and the second grip portion is, inside the hole, a distance which keeps the sensor retained, and outside the hole, a distance which allows the sensor to be released from retention, the latter distance being greater than the distance between the first grip portion and the second grip portion when being inside the hole.

In one implementation, the first grip portion is coupled by a first coupler with the movable section. Given a first angle being defined as an angle constituted by the first coupler and a sliding direction of the movable section, when the first coupler goes outside the hole, the distance between the first grip portion and the second grip portion may be expanded as the first angle increases.

In one implementation, the first coupler is a first open-close bar which is elastic; and the first open-close bar is attached to the movable section so that the first angle equals a predetermined first initial angle when outside the hole. Inside the hole, the first open-close bar may deform so that the first angle becomes smaller than the first initial angle, and when the first open-close bar goes outside the hole, the first open-close bar may be restored from deformation so that the first angle becomes as large as the first initial angle.

In one implementation, the second grip portion is coupled by a second coupler with the movable section. Given a second angle being defined as an angle constituted by the second coupler and the sliding direction of the movable section, when the second coupler goes outside the hole, the distance between the first grip portion and the second grip portion may be expanded as the second angle increases.

In one implementation, the second coupler is a second open-close bar which is elastic; and the second open-close bar is attached to the movable section so that the second angle equals a predetermined second initial angle when outside the hole. Inside the hole, the second open-close bar may deform so that the second angle becomes smaller than the second initial angle, and when the second open-close bar goes outside the hole, the second open-close bar may be restored from deformation so that the second angle becomes as large as the second initial angle.

At least one of the first coupler and the second coupler may be provided so as not to be in contact with an inner wall of the hole when inside the hole.

A sensor embedding device according to one implementation further comprises a sensor retention releaser to release the sensor from retention by the sensor retainer. The sensor retention releaser may expand the distance between the first grip portion and the second grip portion to release the sensor from retention by the sensor retainer.

In one implementation, the sensor retention releaser comprises a push bar; the first grip portion is coupled by the first open-close bar with the movable section; and the push bar is located closer to the center of the hole than is the first open-close bar. The sensor retention releaser may expand the distance between the first grip portion and the second grip portion as the push bar pushes back the first open-close bar toward an outer periphery of the hole.

In one implementation, the second grip portion is coupled by the second open-close bar with the movable section; and the push bar is located closer to the center of the hole than is the second open-close bar. The sensor retention releaser may expand the distance between the first grip portion and the second grip portion as the push bar pushes back the second open-close bar toward the outer periphery of the hole.

In one implementation, the movable section includes a support shaft which is hollow. The support shaft may be inserted in the hole so as to slide inside the hole; and the push bar may be inserted into the support shaft so as to slide inside the support shaft.

In one implementation, the first grip portion is located by a first side face of the sensor; and the second grip portion is located by an opposite side of the sensor from the first side face.

In one implementation, the first grip portion is located on a side where the sensing region of the sensor is situated; and the second grip portion is located on an opposite side from the side where the sensing region of the sensor is situated.

In one implementation, at least one of the first grip portion and the second grip portion has a semicylindrical shape.

In one implementation, the first grip portion and the second grip portion are in contact with each other when retaining the sensor.

The needle may be inserted via a surface of the subject. The predetermined direction may be toward the surface of the subject.

In one implementation, the sensor is used to measure or monitor an analyte within a biological body by using an optical technique. The optical technique may be surface-enhanced Raman scattering spectroscopy or surface-enhanced fluorescence spectroscopy.

A sensor embedding device according to one implementation further comprises a plunger, a needle guide, a cylinder into which the plunger is to be inserted, a contact portion, a pulled-out needle fixture, a pulled-out sensor retainer fixture, and a checker. The plunger retains the needle, the movable section, and the sensor retainer. The needle guide retains the needle, the movable section, and the sensor retainer in a state where the needle, the movable section, and the sensor retainer have been moved to a predetermined position with a slide of the plunger. The contact portion is attached at a predetermined angle to the cylinder, the contact portion having a hole through which the needle passes, and the contact portion coming in contact with a surface of the subject. The pulled-out needle fixture causes the needle having been pulled out from inside the subject to be fixed in the plunger. The pulled-out sensor retainer fixture causes the movable section and sensor retainer having been pulled out from inside the subject to be fixed in the plunger. The checker informs a user using the sensor embedding device of a success or failure of embedment.

The contact portion may comprise an attachment with which to attach the contact portion to the surface of the subject.

A sensor embedding system according to another implementation of the present invention is a sensor embedding system for embedding a sensor in a subject. The sensor embedding system according to another implementation of the present invention comprises the sensor and any of the above sensor embedding devices. The sensor includes a sensing region for detecting a state of the subject and a retained portion. The sensor becomes retained as the retained portion is sandwiched between the first grip portion and the second grip portion.

In one implementation, a recess is formed in the first grip portion and the second grip portion. The sensor may become retained as the retained portion of the sensor becomes sandwiched in the recess of the first grip portion and in the recess of the second grip portion.

In one implementation, the sensor is a sensor chip having a plate shape. The sensing region may be formed in a portion of a principal face of the sensor chip; and the retained portion may be a portion of the sensor chip where the sensing region is not formed.

Hereinafter, with reference to the drawings, embodiments of the present invention will be described in detail. In the following description, component elements of substantially identical functions will be denoted by common reference numerals, with their descriptions occasionally omitted.

Figure 20:
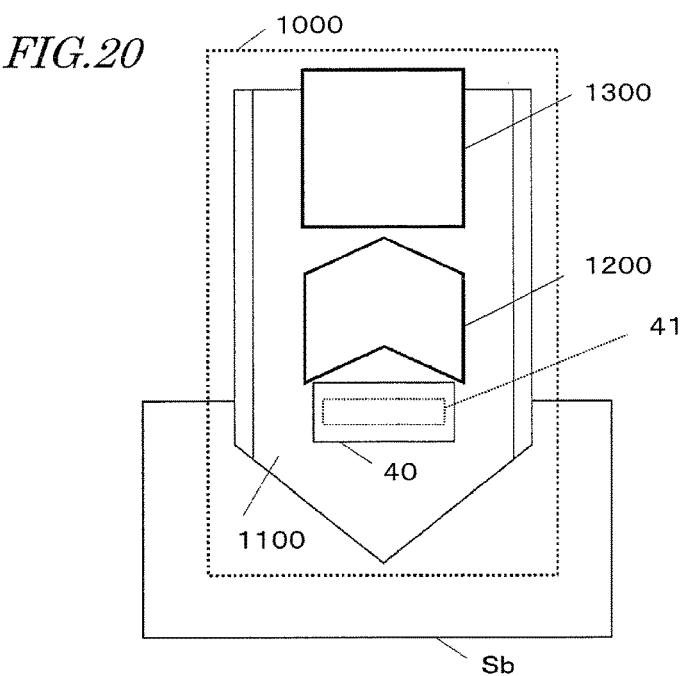
FIG. 20 is a diagram showing in outline a sensor embedding device 1000 according to an illustrative embodiment of the present disclosure.

FIG. 20 is a diagram showing in outline a sensor embedding device 1000 according to an illustrative embodiment of the present disclosure. The sensor embedding device 1000 according to an illustrative embodiment of the present disclosure embeds a sensor 40 in a subject Sb. The sensor 40 has a sensing region 41 for detecting the state of the subject.

The sensor embedding device 1000 includes a needle 1100, a sensor retainer 1200, and a movable section 1300. The needle 1100 has a hole. The needle 1100 is to be inserted into the subject. The sensor retainer 1200 retains the sensor 40 so that the sensor 40 will be embedded inside the subject Sb in such a manner that the sensing region 41 is oriented in a predetermined direction. The movable section 1300 slides the sensor retainer 1200 inside the hole, thus causing the sensor 40 to move into the subject Sb.

With the above construction, a sensor 40 can be embedded inside a subject Sb in such a manner that its sensing region 41 is oriented in a predetermined direction. As a result, the sensor can be embedded in such a manner that the sensor surface having the sensing region is oriented toward the skin surface of a biological body, for example.

Hereinafter, illustrative examples of the sensor embedding device will be described as Embodiments 1 to 8.

Embodiment 1

With reference to FIG. 1 to FIG. 7, Embodiment 1 of the present disclosure will be described. As the subject, Embodiment 1 illustrates a biological body (e.g., a human or animal body).

FIG. 1 is an exploded view showing an exemplary construction of a sensor embedding device 100 according to Embodiment 1 of the present disclosure. For reference's sake, FIG. 1 illustrates the X axis, the Y axis, and the Z axis, which are orthogonal to one another. The X axis, the Y axis, or the Z axis may also be illustrated in other drawings as well.

The sensor embedding device 100 shown in FIG. 1 includes a plunger unit 80, a cylinder unit 57, a body unit 60, and a detector 70.

In the illustrated example, the plunger unit 80 includes a sensor-retaining unit 20, a needle unit 30, and a plunger 10.

The plunger 10 has sensor-retaining unit setting holes 15 at two places that are symmetric in terms of right and left. The sensor-retaining unit 20 includes a sensor-retaining rod 21 and a sensor-retaining rod fixture 22. The sensor-retaining rod fixture 22 is provided at the tail end of the sensor-retaining rod 21. The sensor-retaining rod fixture 22 has immobilizing tabs 24 and a needle unit coupling surface 23 provided thereon. By fitting the immobilizing tabs 24 in the sensor-retaining unit setting holes 15, the sensor-retaining unit 20 becomes fixed in the plunger 10.

Moreover, the plunger 10 includes a needle unit guide slit 14, needle unit setting holes 12, needle unit pullback release slits 13. Note that two needle unit setting holes 12 and two needle unit pullback release slits 13 are formed in the plunger 10. The needle unit setting holes 12, and the needle unit pullback release slits 13, are located in symmetric positions in terms of right and left on the plunger 10.

The needle unit 30 includes needle unit retention tabs 36, a needle 32, sensor-retaining unit release tabs 37, a guide 35, and a slide lever 34. As the needle unit retention tabs 36 are fitted in the needle unit setting holes 12, the needle unit 30 becomes fixed in the plunger 10. The needle 32 has a needle hole 31 through which the sensor 40 and the sensor-retaining rod 21 are to move inside.

The cylinder unit 57 has a needle unit attachment slit 56, a slit 51, a finger rest 52 for providing rest when the plunger unit 80 is to be pressed in, guide bumps 53 with which the cylinder unit 57 is to be attached to the body unit 60, locking tabs 54, and a cylinder 50. The body unit 60 has guide grooves 61 for allowing the cylinder unit 57 to become attached, locking grooves 62, detector attachment tabs 63, and an embedment check window 64. As the guide bumps 53 are fitted in the guide grooves 61 and the locking tabs 54 are fitted in the locking grooves 62, the cylinder unit 57 becomes coupled with the body unit 60.

On the upper face of the detector 70, a display 73 and a confirmation button 72 are provided. On the side faces of the detector 70, detector setting grooves 71 are provided. As the detector attachment tabs 63 are fitted in the detector setting grooves 71, the detector 70 becomes coupled with the body unit 60.

Figure 2:
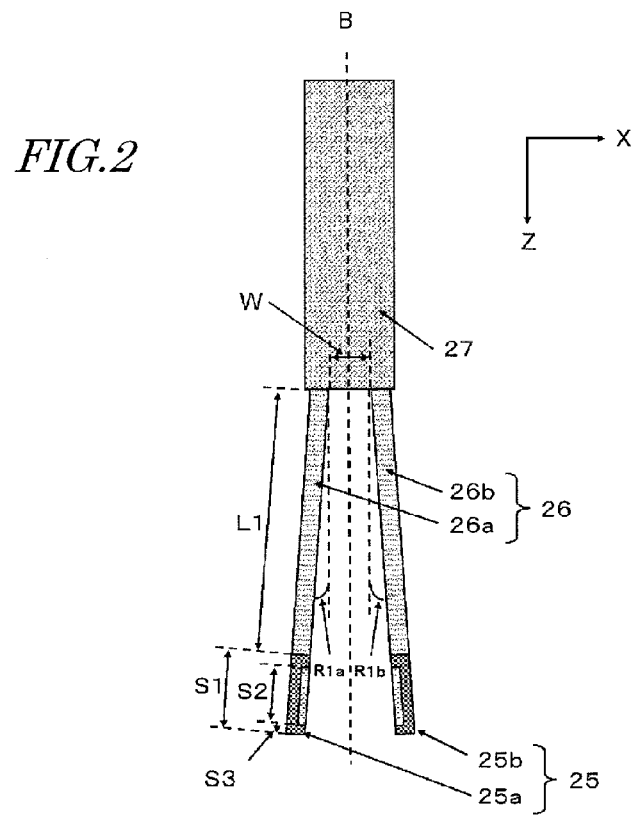
FIG. 2 is an X-Z cross-sectional view of a sensor-retaining rod 21 according to Embodiment 1 of the present disclosure.

FIG. 2 is a schematic cross-sectional view when the sensor-retaining rod 21 is cut along a plane which is parallel to the X-Z plane (see FIG. 1). As shown in FIG. 2, the sensor-retaining rod 21 includes a support shaft 27, a pair of open-close bars 26, and a sensor grip 25. In Embodiment 1, the sensor retainer is constituted by the pair of open-close bars 26 and the sensor grip 25. As shown in the figure, the sensor grip 25 includes a first grip portion 25a and a second grip portion 25b. In Embodiment 1, the sensor retainer retains the sensor by sandwiching the sensor in between the first grip portion and the second grip portion. In the illustrated example, the pair of open-close bars 26 include a first open-close bar 26a (first coupler) and a second open-close bar 26b (second coupler).

The present embodiment will illustrate a construction for the support shaft 27, the open-close bars 26, and the sensor grip 25 in the case where a sensor 40 measuring 1 mm×1 mm and a thickness of 0.2 mm is to be embedded. However, the size of the sensor 40 and the construction of the support shaft 27, the open-close bars 26, and the sensor grip 25 are not limited to this example. Depending on the size of the sensor 40, the construction may be altered as appropriate.

The open-close bars 26 shown in FIG. 2 have a length (L1) of e.g. 5 mm. The support shaft 27 may have a cylindrical shape. The support shaft 27 is designed with a diameter that permits friction-free movement inside the needle. In the present embodiment, the diameter of the support shaft 27 is e.g. 1.65 mm.

One end of each open-close bar 26 is attached to the support shaft 27, within a circular side face of the support shaft 27, for example. At the place where the open-close bars 26 are attached to the support shaft 27, there is an interspace (W) of e.g. about 0.8 mm between the first open-close bar 26a and the second open-close bar 26b.

The first angle (R1a), which is an angle constituted by the first open-close bar 26a and the center line B of the support shaft 27, is set to e.g. about 4 degrees, this defining a first initial angle. Moreover, the second angle (R1b), which is an angle constituted by the second open-close bar 26b and the center line B of the support shaft 27 is set to e.g. about 4 degrees, this defining a second initial angle. The length L1, the first initial angle, and the second initial angle may have any values that permit fixing and freeing of the sensor 40, without being limited to specific values.

Figure 3:
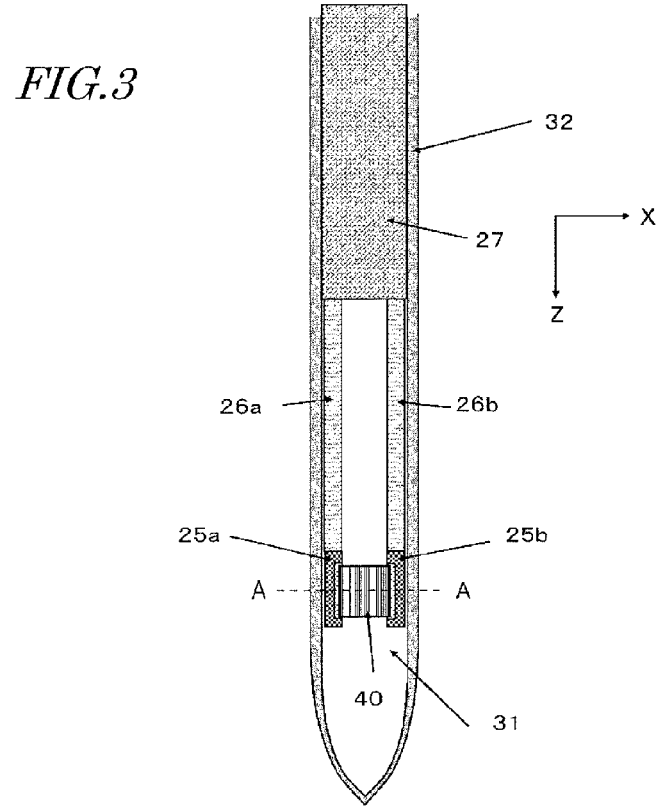
FIG. 3 is an X-Z cross-sectional view of the sensor-retaining rod 21 and a needle 32 according to Embodiment 1 of the present disclosure when the sensor-retaining rod 21 is placed in a needle hole 31.

FIG. 3 is a schematic cross-sectional view showing the sensor-retaining rod 21 and the needle 32 as being cut along a plane which is parallel to the X-Z plane, when the sensor-retaining rod 21 is placed in the needle hole 31. As illustrated in FIG. 3, in Embodiment 1, the first grip portion 25a is located by the first side face of the sensor. The second grip portion 25b is located by the opposite side of the sensor from the first side face.

The needle 32 may have a thickness of e.g. 14 G. That is, it may have an inner diameter of 1.69 mm and an outer diameter of 2.11 mm.

By placing the sensor-retaining rod 21 in the needle hole 31, stress acts on the first open-close bar 26a and the second open-close bar 26b to deform the open-close bars 26. In the illustrated example, the pair of open-close bars 26 are substantially parallel. In other words, in the illustrated example, the first angle R1a (see FIG. 2) is about 0 degrees inside the needle hole 31. Moreover, the second angle R1b (see FIG. 2) is about 0 degrees inside the needle hole 31. As a result, the sensor 40 is fixed by the sensor grip 25.

Next, with reference to FIG. 4, a method of fixing the sensor 40 with the sensor grip 25 will be described.

Figure 4:
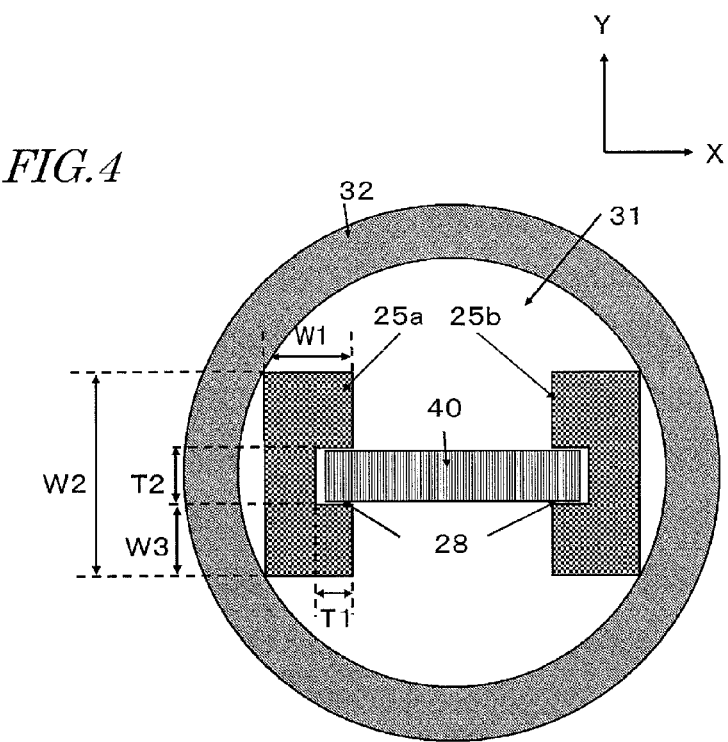
FIG. 4 is an X-Y cross-sectional view of a sensor grip 25 according to Embodiment 1 of the present disclosure.

FIG. 4 is a schematic cross-sectional view (a cross-sectional view taken along line A-A shown in FIG. 3) when the sensor grip 25 is cut along a plane which is parallel to the X-Y plane. In the example shown in FIG. 4, the sensor grip 25 (i.e., the first grip portion 25a and the second grip portion 25b) has a recess 28 into which the sensor 40 is to be fitted.

In the illustrated example, the sensor grip 25 has a width (W1) of 0.35 mm along the X direction and a width (W2) of 0.8 mm along the Y direction. The recess 28 has a depth (T1) of 0.15 mm and a width (T2) of 0.2 mm. The thickness (W3) from the bottom face of the sensor grip 25 to the recess 28 is 0.3 mm. The width T2 is slightly larger than the sensor thickness. Herein, the open-close bars 26 (i.e., the first open-close bar 26a and the second open-close bar 26b) each have a prism shape, with a width of 0.35 mm along the X direction and a width of 0.8 mm along the Y direction. Note that the shape of the open-close bars 26 is not limited to prisms. The shape of the open-close bars 26 may be prisms, cylinders, or semicylinders.

The materials of the open-close bars 26 and the sensor grip 25 are not limited to any particular materials so long as they are elastic and capable of being processed. Examples of the materials of the open-close bars 26 and the sensor grip 25 include metals, alloys, resins, etc. Examples of processing methods for the support shaft 27, the open-close bars 26, and the sensor grip 25 include cutting processes, laser processes, etc. The processing methods are not limited to any particular methods so long as they are capable of processing these materials.

The recess 28 has a width (S2) of e.g. 1.1 mm along the Z direction (see FIG. 2). The sensor grip 25 has a width (S1) of e.g. 1.5 mm along the Z direction (see FIG. 2). So long as the sensor 40 is able to be fixed, the values of S2 and S1 are not limited respectively to 1.1 mm and 1.5 mm.

Figure 5:
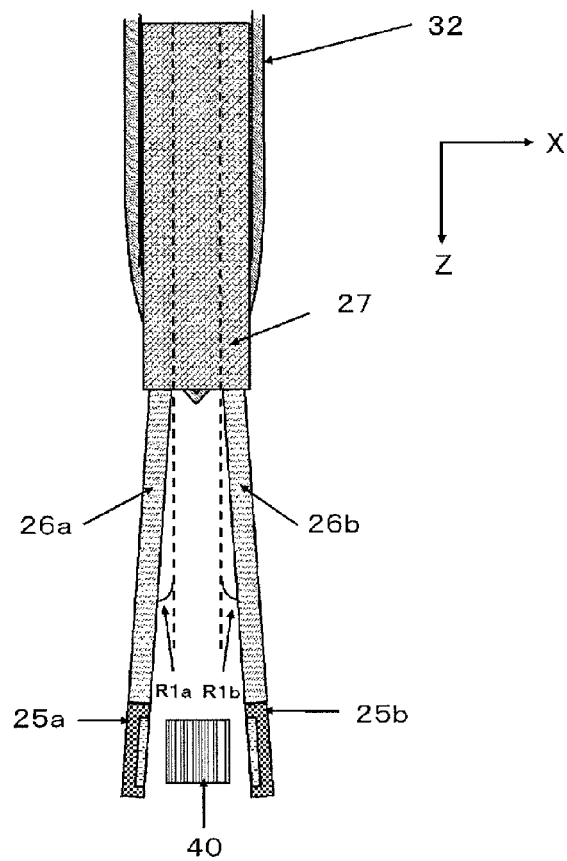
FIG. 5 is an X-Z cross-sectional view of the sensor grip 25 and open-close bars 26 in a state where they are outside the needle hole 31 of the needle 32.

FIG. 5 is a schematic cross-sectional view of the sensor grip 25 and the open-close bars 26 as being cut along a plane which is parallel to the X-Z plane, in a state where they are outside the needle hole 31 of the needle 32.

In Embodiment 1, when the sensor grip 25 and the open-close bars 26 go outside the needle hole 31, restoration from deformation occurs due to elasticity of the first open-close bar 26a and the second open-close bar 26b, whereby the open-close bars 26 become spread. For example, when the first open-close bars 26a go outside the needle hole 31, the first angle R1a becomes as large as the first initial angle (about 4 degrees). When the second open-close bar 26 goes outside the needle hole 31, the second angle R1b becomes as large as the second initial angle (about 4 degrees). As a result, the sensor 40 is freed from the sensor grip 25.

As described above, in Embodiment 1, the sensor is released from retention when the sensor retainer goes outside the hole of the needle.

In Embodiment 1, inside the hole, the distance between the first grip portion 25a and the second grip portion 25b is a distance which keeps the sensor retained. Outside the hole, the distance between the first grip portion 25a and the second grip portion 25b is a distance which allows the sensor to be released from retention. The distance which allows the sensor to be released from retention is greater than the distance between the first grip portion 25a and the second grip portion 25b when inside the hole. In Embodiment 1, owing to the first open-close bar 26a serving as the first coupler, the first grip portion 25a is coupled with the support shaft 27, which is a portion of the movable section. When the first open-close bar 26a serving as the first coupler goes outside the hole, the first angle R1a increases. This increases the distance between the first grip portion 25a and the second grip portion 25b. Note that the first angle is the angle constituted by the first coupler and the sliding direction (the direction of the center line B of the support shaft 27; see FIG. 2) of the movable section.

In Embodiment 1, the first open-close bar 26a is elastic. Moreover, the first open-close bar 26a is attached to the support shaft 27, which is a portion of the movable section, in such a manner that the first angle R1a equals the predetermined first initial angle when outside the hole. Under this condition, when inside the hole, the first open-close bar 26a deforms so that the first angle R1a is smaller than the first initial angle. Then, when the first open-close bar 26a goes outside the hole, the first open-close bar 26a is restored from deformation, whereby the first angle R1a becomes as large as the first initial angle.

Furthermore, in Embodiment 1, owing to the second open-close bar 26b serving as the second coupler, the second grip portion 25b is coupled with the support shaft 27, which is a portion of the movable section. When the second open-close bar 26b serving as the second coupler goes outside the hole, the second angle R1b increases. This increases the distance between the first grip portion 25a and the second grip portion 25b. Note that the second angle is the angle constituted by the second coupler and the sliding direction (the direction of the center line B of the support shaft 27; see FIG. 2) of the movable section.

In Embodiment 1, the second open-close bar 26b is elastic. Moreover, the second open-close bar 26b is attached to the support shaft 27, which is a portion of the movable section, in such a manner that the second angle R1b equals the predetermined second initial angle when outside the hole. Under this condition, when inside the hole, the second open-close bar 26b deforms so that the second angle R1b is smaller than the second initial angle. Then, when the second open-close bar 26b goes outside the hole, the second open-close bar 26b is restored from deformation, whereby the second angle R1b becomes as large as the second initial angle.

Figure 6:
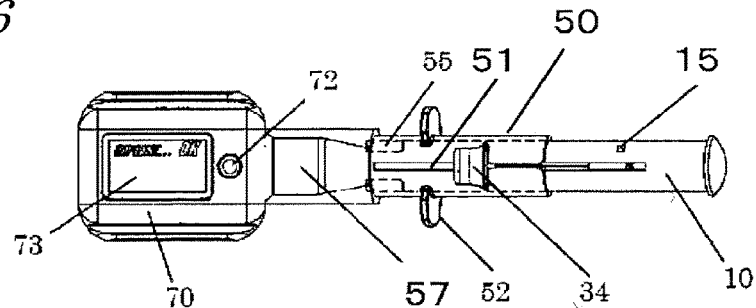
FIG. 6 is an upper plan view of the sensor embedding device 100 according to Embodiment 1 of the present disclosure.
Figure 6:
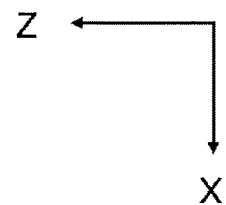

FIG. 6 is an upper plan view of the sensor embedding device 100. In the example shown in FIG. 6, ribs 55 for stopping the needle unit 30 from sliding are formed inside the cylinder 50.

Figure 7:
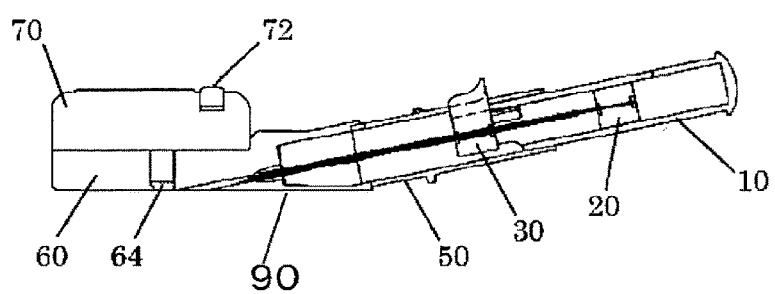
FIG. 7 is a side cross-sectional view of the sensor embedding device 100 according to Embodiment 1 of the present disclosure.
Figure 7:
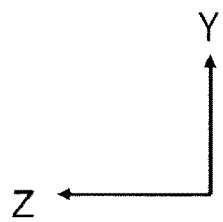

FIG. 7 is a side cross-sectional view of the sensor embedding device 100. In the present embodiment, as shown in FIG. 7, the cylinder 50 is inclined with respect to the contact surface 90. The angle constituted by the cylinder 50 and the contact surface 90 is e.g. about 11 degrees. Herein, the ribs 55 are arranged so that the length of the needle 32 allowed to be inserted into a biological body would be about 15 mm. With the above-described construction, the sensor 40 can be embedded to a depth of about 1 mm inside a biological body, for example. In order to fix the sensor embedding device 100 to a biological body, the contact surface 90 may have a tacky portion with a cover sheet (not shown).

Note that the sensor 40 may be embedded under the skin of the biological body. Moreover, the contact surface 90 may come in contact with the skin of the biological body.

See FIG. 1 again. At use, the sensor-retaining unit 20 having the sensor-retaining rod fixture 22 with immobilizing tabs 24 provided on side faces is inserted into the plunger 10, in such a manner that the immobilizing tabs 24 are engaged in the sensor-retaining unit setting holes 15 provided at the rear of the plunger 10. Next, the sensor 40 is sandwiched by the sensor grip 25, and then the sensor-retaining rod 21 is inserted in the needle hole 31, which is opened in the needle 32 of the needle unit 30. By engaging the needle unit retention tabs 36 provided on side faces of the needle unit 30 in the needle unit setting holes 12 provided at the front of the plunger 10, the needle unit 30 becomes retained by the plunger 10.

The guidepiece 35 of the needle unit 30 is inserted in the needle unit attachment slit 56 of the cylinder 50, until the plunger 10 becomes fixed as the guidepiece 35 is fitted in the slit 51. Thus, the plunger 10 retaining the sensor-retaining unit 20 and the needle unit 30 is now retained by the cylinder unit 57.

The guide grooves 61 of the body unit 60 are aligned with the guide bumps 53 of the cylinder unit 57, and the cylinder unit 57 retaining the plunger 10 is pressed in until the locking grooves 62 of the body unit 60 become mated with the locking tabs 54 of the cylinder unit 57, whereby the cylinder unit 57 and the body unit 60 are coupled. After coupling the cylinder unit 57 and the body unit 60, the detector 70 is pressed into the body unit 60 so that the detector attachment tabs 63 of the body unit 60 become mated with the detector setting grooves 71 of the detector 70. Thus, the detector 70 and the body unit 60 are coupled. In this manner, the plunger unit 80, the cylinder unit 57, the body unit 60, and the detector 70 are coupled (see FIG. 6).

Next, with reference to the drawings, an operation when the sensor embedding device 100 of the present embodiment embeds the sensor 40 will be described. When embedding the sensor 40, as necessary, the user may remove the cover sheet to allow the contact surface 90 to be attached to the biological surface with the tacky portion.

See FIG. 6 and FIG. 7. While resting a finger on the finger rest 52 provided midway on the cylinder unit 57, the rear end of the plunger 10 is pushed with a thumb. As a result of this, the plunger 10 slides within the cylinder 50, while the needle unit 30 and the sensor-retaining unit 20 fixed to the plunger 10 also slide concurrently. Thus, the needle 32 protrudes from a hole in the contact surface 90 to be inserted into a biological body.

At this time, as the needle unit retention tabs 36 of the needle unit 30 ride onto the ribs 55 in the cylinder 50, the needle unit 30 becomes disengaged from the plunger 10, thus being freed. When the plunger 10 is further pressed in, the sensor-retaining unit 20 fixed on the plunger 10 moves inside the needle hole 31 of the needle unit 30. In other words, the support shaft 27 slides inside the needle hole 31 (see FIG. 3, FIG. 5, etc.). As a result, the sensor grip 25 coupled to the support shaft 27 also slides.

Thus, the sensor grip 25 and the sensor 40 are pushed out of the needle hole 31. At this time, the open-close bars 26 are also forced out of the needle hole 31, and thus the sensor grip 25 spreads out to free the sensor 40.

Next, the finger is taken off the finger rest 52 of the cylinder unit 57, and the slide lever 34 of the needle unit 30 is pulled up. Consequently, the needle 32 exits the biological body, and the needle unit 30 abuts against the needle unit coupling surface 23 of the sensor-retaining unit 20, whereby the sensor-retaining unit 20 and the needle unit 30 become fixed. Moreover, the sensor-retaining unit release tabs 37 provided at the rear of the needle unit 30 causes the sensor-retaining unit 20 to be freed from its fixture to the plunger 10 that has been implemented by the immobilizing tabs 24.

As the slide lever 34 is further pulled up, the needle unit 30 and the sensor-retaining unit 20 are pulled up. As a result, the needle 32 and the sensor-retaining rod 21 become accommodated into the cylinder 50.

According to the present embodiment, in order to check whether the sensor 40 has been properly embedded, the confirmation button 72 on the detector 70 is pushed. Then, the detector 70 radiates laser light onto the biological body. The laser light passes through the check window 64. If the detector 70 detects any light which is reflected from the surface of the sensor 40, the sensor embedding device 100 informs the user of a successful embedment. If light is not detected, the sensor embedding device 100 informs the user of a failure of embedment. The sensor embedding device 100 is detached from the biological body, thus completing the embedment procedure.

Thus, in Embodiment 1, the movable section is constituted by the support shaft 27 and the like. The movable section causes the sensor retainer, which is constituted by the sensor grip 25 and the like, to slide inside the needle hole 31, thus moving the sensor into the subject.

Moreover, in Embodiment 1, the needle is inserted via the surface of the subject. The sensor retainer retains the sensor so that, inside the subject, the sensing region of the sensor is oriented toward the surface of the subject. As referred to herein, the surface of the subject may be the skin of the biological body.

In Embodiment 1, the sensor may be used in an optical technique for measuring or monitoring an analyte (object of analysis) within a biological body. In this case, the optical technique may be surface-enhanced Raman scattering spectroscopy, surface-enhanced fluorescence spectroscopy, or the like.

In the above-described example, the sensor embedding device includes a plunger, a needle guide, a cylinder into which the plunger is to be inserted, a contact portion, a pulled-out needle fixture (first fixture), a pulled-out sensor retainer fixture (second fixture), and a checker. The plunger retains a needle, a movable section, and a sensor retainer. The needle guide retains the needle, the movable section, and the sensor retainer, especially in a state where the needle, the movable section, and the sensor retainer have been moved to a predetermined position with a slide of the plunger. The contact portion, which comes in contact with the surface of a subject, is attached to the cylinder at a predetermined angle, the contact portion having a hole through which the needle is allowed to pass. The pulled-out needle fixture causes the needle having been pulled out from inside the subject to be fixed in the plunger. The pulled-out sensor retainer fixture causes the movable section and sensor retainer having been pulled out from inside the subject to be fixed in the plunger. The checker informs the user of a success or failure of embedment.

In Embodiment 1, the needle guide is exemplified by a construction including the slit 51, the ribs 55, the needle unit attachment slit 56, and so on. In Embodiment 1, the contact portion is exemplified by the contact surface 90. In Embodiment 1, the pulled-out needle fixture is exemplified by a construction including the slide lever 34, the guide 35, and so on. In Embodiment 1, the pulled-out sensor retainer fixture is exemplified by a construction including the sensor-retaining unit release tabs 37, the needle unit coupling surface 23, and so on. In Embodiment 1, the checker is exemplified by the detector 70.

The sensor embedding device according to Embodiment 1 may include an attachment with which to attach the contact portion onto the surface of the subject. In Embodiment 1, the attachment is exemplified by the tacky portion.

As described above, by using the sensor embedding device 100 of Embodiment 1, a sensor can be embedded at a predetermined depth. Furthermore, the sensor can be embedded in such a manner that its sensor surface is oriented toward the biological surface.

Embodiment 2

Figure 8:
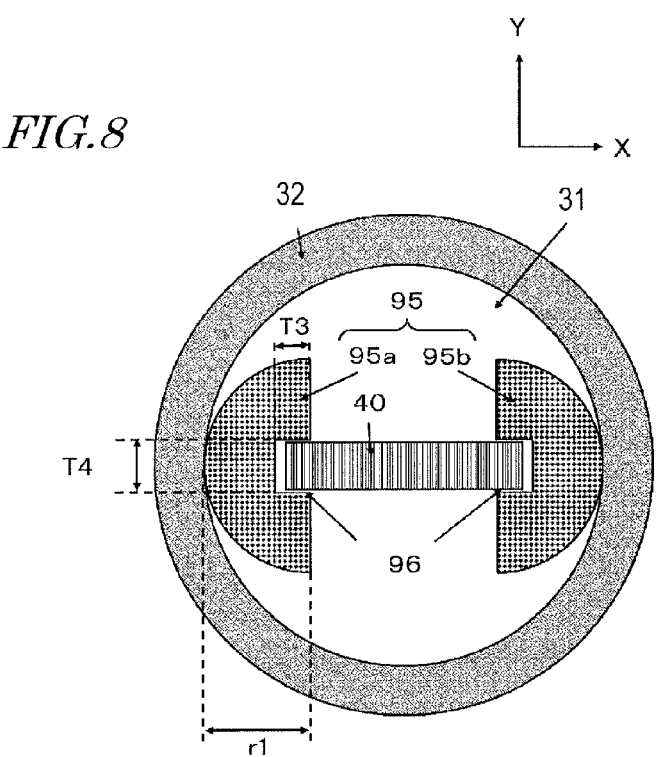
FIG. 8 is an X-Y cross-sectional view of a sensor grip 95 according to Embodiment 2 of the present disclosure.

With reference to FIG. 8, Embodiment 2 of the present disclosure will be described.

The present embodiment differs from Embodiment 1 in that a sensor grip 95 of the present embodiment has a different shape from that of the sensor grip 25 of Embodiment 1. Other than the sensor grip 95, the same construction as that of Embodiment 1 may be adopted. Therefore, common reference numerals will be given to component elements having substantially identical functions.

FIG. 8 is a schematic cross-sectional view when the sensor grip 95 is cut along a plane which is parallel to the X-Y plane. Similarly to FIG. 4, FIG. 8 corresponds to a cross-sectional view taken along line A-A shown in FIG. 3.

Similarly to Embodiment 1, the present embodiment will illustrate a construction for the sensor grip 95 in the case where a sensor 40 measuring 1 mm×1 mm and a thickness of 0.2 mm is to be embedded. However, the size of the sensor 40 and the construction of the support shaft 27, the open-close bars 26, and the sensor grip 95 are not limited to this example. Depending on the size of the sensor 40, the construction may be altered as appropriate.

In the example shown in FIG. 8, the sensor grip 95 includes a first grip portion 95a and a second grip portion 95b. As shown in the figure, the first grip portion 95a and the second grip portion 95b each have a semicylindrical shape. The sensor grip 95 has a recess 96 into which the sensor 40 is to be fitted.

The needle 32 may have a thickness of e.g. 14 G. That is, it may have an inner diameter of 1.69 mm and an outer diameter of 2.11 mm.

In the construction illustrated in FIG. 8, the sensor grip 95 has a radius of curvature (r1) of 0.45 mm. The recess 96 has a depth (T3) of 0.15 mm and a width (T4) of 0.2 mm. The width T4 is slightly larger than the sensor thickness.

The recess 96 has a width of e.g. 1.1 mm along the Z direction, and the sensor grip 95 has a width of e.g. 1.5 mm along the Z direction. As in Embodiment 1, so long as the sensor 40 is able to be fixed, the width of the recess 96 along the Z direction and the width of the sensor grip 95 along the Z direction are not limited respectively to 1.1 mm and 1.5 mm.

Other component elements and the operation when embedding the sensor 40 may be identical to those of Embodiment 1. Therefore, their description will be omitted.

In the sensor embedding device of Embodiment 2, the first grip portion 95a and the second grip portion 95b have semicylindrical shapes. The sensor embedding device of Embodiment 2 may be arranged so that at least one of the first grip portion 95a and the second grip portion 95b has a semicylindrical shape.

Thus, in Embodiment 2, at least one of the first grip portion 95a and the second grip portion 95b is semicylindrical. This can decrease the number of corners of the sensor grip 95 relative to prism shapes and the like. Thus, damage to the subject (e.g. biological tissue) during embedment can be reduced.

Embodiment 3

With reference to FIG. 9 to FIG. 12, Embodiment 3 of the present disclosure will be described.

The present embodiment differs from Embodiments 1 and 2 in that a sensor grip 105 of the present embodiment has a different shape from those of the sensor grip 25 of Embodiment 1 and the sensor grip 95 of Embodiment 2. Other than the sensor grip 105, the same construction as that of Embodiment 1 may be adopted. Therefore, common reference numerals will be given to component elements having substantially identical functions.

Figure 9:
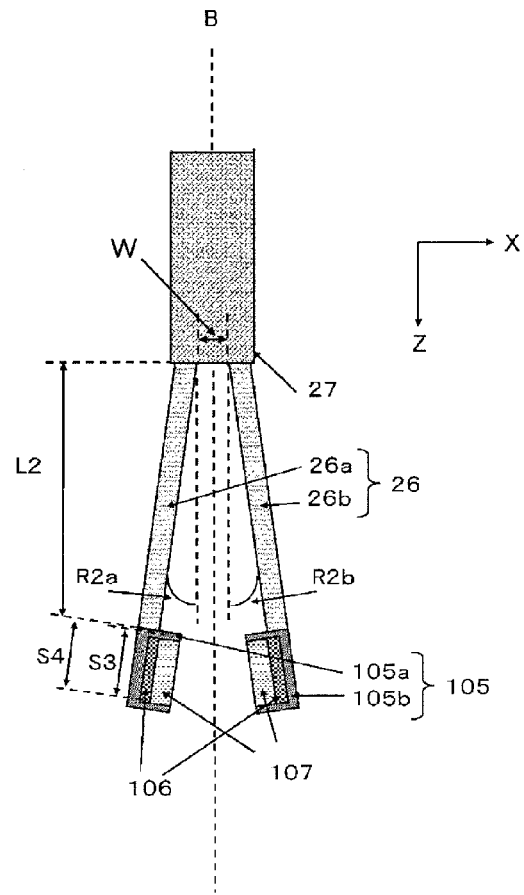
FIG. 9 is an X-Z cross-sectional view of a sensor-retaining rod 21 according to Embodiment 3 of the present disclosure.

FIG. 9 is a schematic cross-sectional view when the sensor-retaining rod 21 is cut along a plane which is parallel to the X-Z plane (see FIG. 1). As shown in FIG. 9, the sensor-retaining rod 21 of the present embodiment includes a support shaft 27, a pair of open-close bars 26, and a sensor grip 105.

The sensor grip 105 includes a first grip portion 105a and a second grip portion 105b. As shown in the figure, each of the first grip portion 105a and the second grip portion 105b has two recesses 106 and 107.

The present embodiment will illustrate a construction for the support shaft 27, the open-close bars 26, and the sensor grip 105 in the case where a sensor 40 measuring 1 mm×1 mm and a thickness of 0.2 mm is to be embedded. However, the size of the sensor 40 and the construction of the support shaft 27, the open-close bars 26, and the sensor grip 105 are not limited to this example. Depending on the size of the sensor 40, the construction may be altered as appropriate.

The open-close bars 26 shown in FIG. 9 have a length (L2) of e.g. 5 mm. Similarly to Embodiment 1, the support shaft 27 may have a cylindrical shape. The support shaft 27 is designed with a diameter that permits friction-free movement inside the needle. In the present embodiment, the diameter of the support shaft 27 is e.g. 1.65 mm.

One end of each open-close bar 26 is attached to the support shaft 27, within a circular side face of the support shaft 27, for example. At the place where the open-close bars 26 are attached to the support shaft 27, there is an interspace (W) of e.g. about 0.8 mm between the first open-close bar 26a and the second open-close bar 26b.

Herein, the first angle (R2a), which is an angle constituted by the first open-close bar 26a and the center line B of the support shaft 27, is set to e.g. about 8 degrees, this defining a first initial angle. Moreover, the second angle (R2b), which is an angle constituted by the second open-close bar 26b and the center line B of the support shaft 27, is set to e.g. about 8 degrees, this defining a second initial angle.

The open-close bars 26 may be shaped similarly to those in Embodiment 1. The length L2, the first initial angle, and the second initial angle may have any values that permit fixing and freeing of the sensor 40, without being limited to specific values.

Figure 10:
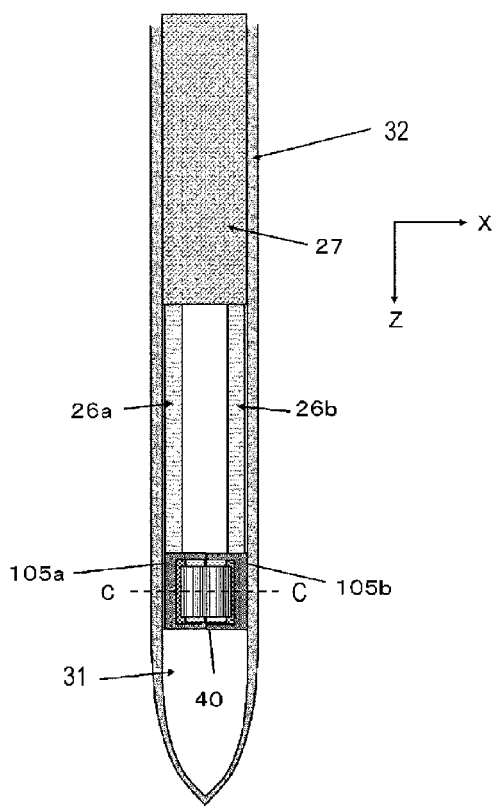
FIG. 10 is an X-Z cross-sectional view of the sensor-retaining rod 21 and a needle 32 according to Embodiment 3 of the present disclosure when the sensor-retaining rod 21 is placed in a needle hole 31.

FIG. 10 is a schematic cross-sectional view of the sensor-retaining rod 21 and the needle 32 as being cut along a plane which is parallel to the X-Z plane, when the sensor-retaining rod 21 of the present embodiment is placed in the needle hole 31.

The needle 32 may have a thickness of e.g. 14 G. That is, it may have an inner diameter of 1.69 mm and an outer diameter of 2.11 mm.

The sensor-retaining rod 21 is placed in the needle hole 31. As a result, stress acts on the first open-close bar 26a and the second open-close bar 26b to deform the open-close bars 26. This causes the pair of open-close bars 26 to become parallel. That is, in the illustrated example, the first angle R2a (see FIG. 9) is about 0 degrees inside the needle hole 31. The second angle R2b (see FIG. 9) is about 0 degrees inside the needle hole 31. As a result, the sensor 40 is fixed by the sensor grip 105.

Figure 11:
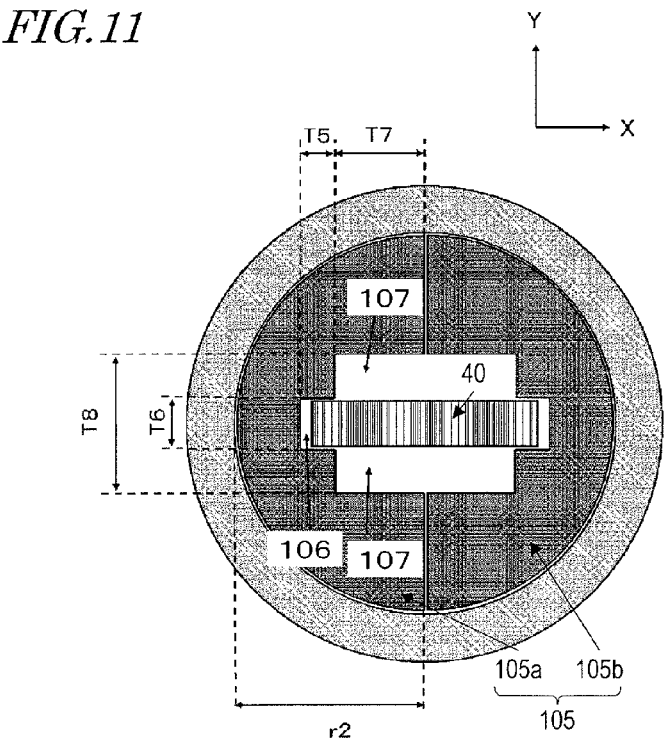
FIG. 11 is an X-Y cross-sectional view of a sensor grip 105 according to Embodiment 3 of the present disclosure.

With reference to FIG. 11, a method of fixing the sensor 40 with the sensor grip 105 will be described.

FIG. 11 is schematic cross-sectional view (a cross-sectional view taken along line C-C shown in FIG. 10) when the sensor grip 105 is cut along a plane which is parallel to the X-Y plane. In the example shown in FIG. 11, the sensor grip 105 (i.e., the first grip portion 105a and the second grip portion 105b) has a recess 106 into which the sensor 40 is to be fitted and a recess 107 for avoiding contact with the sensor surface. The first grip portion 105a and the second grip portion 105b are in contact with each other when retaining the sensor 40.

In the construction illustrated in FIG. 11, the first grip portion 105a and the second grip portion 105b are each semicylindrical. In the illustrated example, the sensor grip 105 has a radius of curvature (r2) of about 0.8 mm. The recess 106 has a depth (T5) of 0.15 mm and a width (T6) of 0.2 mm. The recess 107 has a depth (T7) of about 0.4 mm and a width (T8) of 0.6 mm. The width T6 is slightly larger than the sensor thickness.

Herein, the open-close bars 26 (i.e., the first open-close bar 26a and the second open-close bar 26b) each have a prism shape, with a width of 0.3 mm along the X direction and a width of 0.8 mm along the Y direction.

The materials of the open-close bars 26 and the sensor grip 105 are not limited to any particular materials so long as they are elastic and capable of being processed. Examples of the materials of the open-close bars 26 and the sensor grip 105 include metals, alloys, resins, etc. Examples of processing methods for the support shaft 27, the open-close bars 26, and the sensor grip 105 include cutting processes, laser processes, etc. The processing methods are not limited to any particular methods so long as they are capable of processing these materials.

The recesses 106 and 107 have a width (S3) of e.g. 1.1 mm along the Z direction (see FIG. 9). The sensor grip 105 has a width (S4) of e.g. 1.5 mm along the Z direction (see FIG. 9). So long as the sensor 40 is able to be fixed, the values of S3 and S4 are not limited to respectively 1.1 mm and 1.5 mm.

Figure 12:
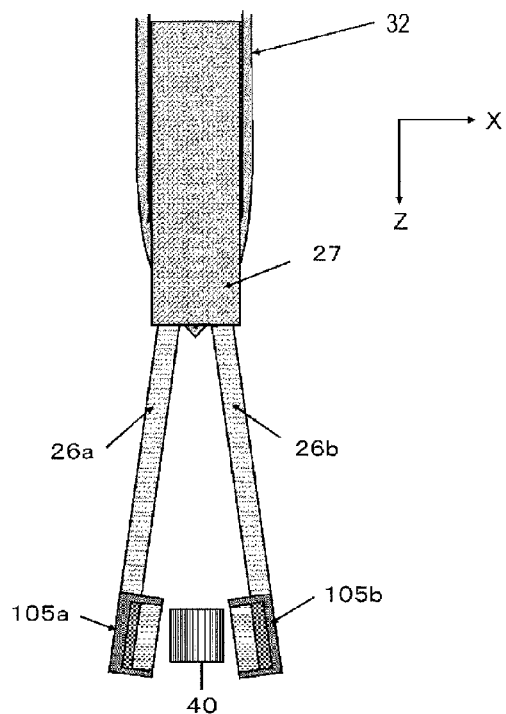
FIG. 12 is an X-Z cross-sectional view of the sensor grip 105 and open-close bars 26 according to Embodiment 3 of the present disclosure in a state where they are outside the needle hole 31 of the needle 32.

FIG. 12 is a schematic cross-sectional view of the sensor grip 105 and the open-close bars 26 as being cut along a plane which is parallel to the X-Z plane, in a state where they are outside the needle hole 31 of the needle 32.

In Embodiment 3, when the sensor grip 105 and the open-close bars 26 go outside the needle hole 31, restoration from deformation occurs due to elasticity of the first open-close bar 26a and the second open-close bar 26b, whereby the open-close bars 26 become spread. For example, when the first open-close bars 26a go outside the needle hole 31, the first angle R2a becomes as large as the first initial angle (about 8 degrees). When the second open-close bar 26 goes outside the needle hole 31, the second angle R2b becomes as large as the second initial angle (about 8 degrees). As a result, the sensor 40 is freed from the sensor grip 105.

Other component elements and the operation when embedding the sensor 40 may be identical to those of Embodiment 1. Therefore, their description will be omitted.

As described above, in the sensor embedding device of Embodiment 3, the first grip portion 105a and the second grip portion 105b are in contact with each other when retaining the sensor. Thus, in Embodiment 3, the first grip portion 105a and the second grip portion 105b (constituting the sensor grip 105) are capable of being in contact with each other. This allows the sensor 40 to be fixed in a more stable manner.

Embodiment 4

Figure 13:
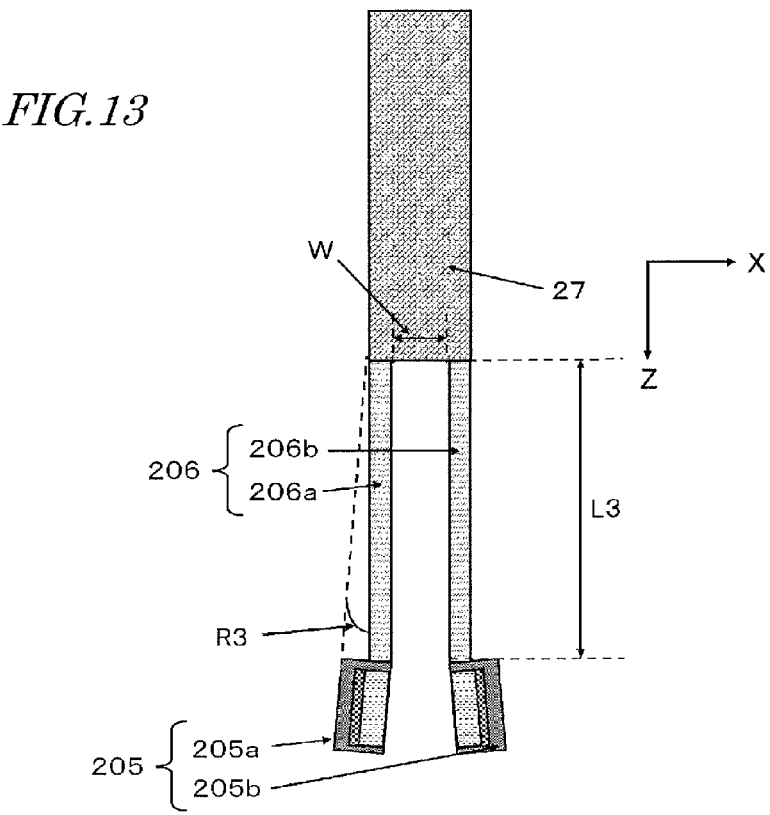
FIG. 13 is an X-Z cross-sectional view of a sensor-retaining rod 21 according to Embodiment 4 of the present disclosure.
Figure 14:
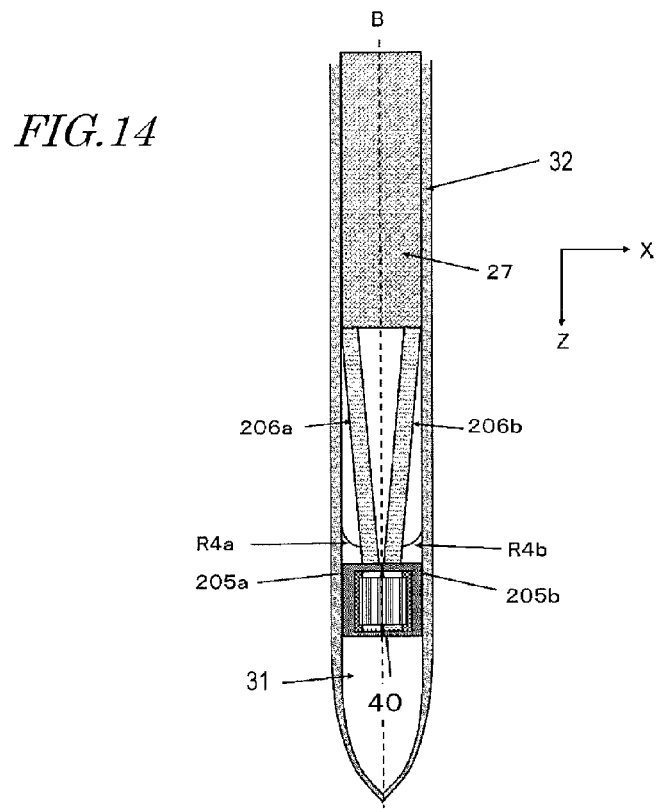
FIG. 14 is an X-Z cross-sectional view of the sensor-retaining rod 21 and a needle 32 according to Embodiment 4 of the present disclosure when the sensor-retaining rod 21 is placed in a needle hole 31.
Figure 15:
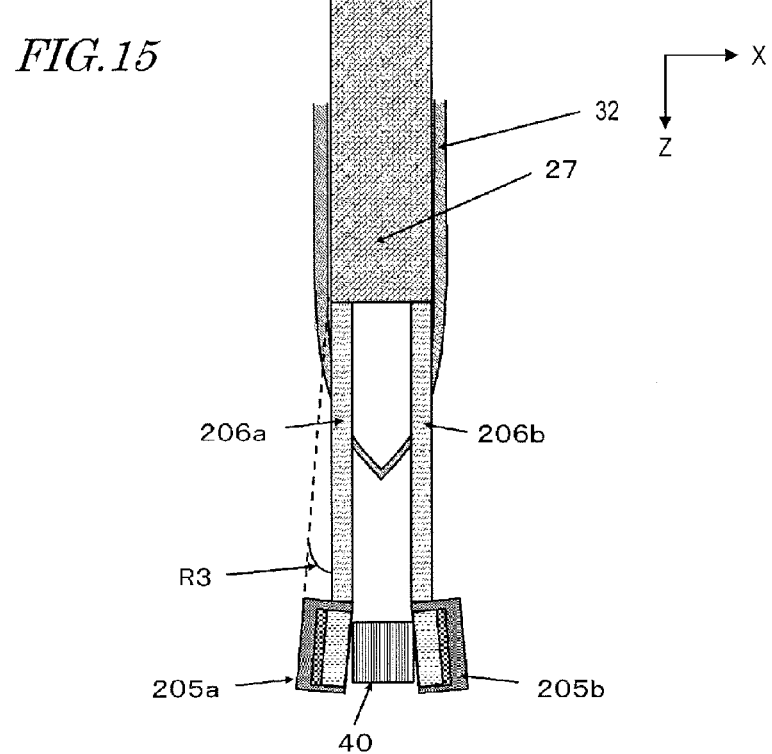
FIG. 15 is an X-Z cross-sectional view of a sensor grip 205 and open-close bars 206 according to Embodiment 4 of the present disclosure in a state where they are outside the needle hole 31 of the needle 32.

With reference to FIG. 13 to FIG. 15, Embodiment 4 of the present disclosure will be described.

A difference between the present embodiment and Embodiment 1 is that the open-close bars 206 and the sensor grip 205 of the present embodiment are respectively different in construction from the open-close bars 26 and the sensor grip 25 of Embodiment 1. Other than the open-close bars 206 and the sensor grip 205, the same construction as that of Embodiment 1 may be adopted. Therefore, common reference numerals will be given to component elements having substantially identical functions.

FIG. 13 is a schematic cross-sectional view of the sensor-retaining rod 21 of the present embodiment as being cut along a plane which is parallel to the X-Z plane (see FIG. 1). As shown in FIG. 13, the sensor-retaining rod 21 of the present embodiment includes a support shaft 27, a pair of open-close bars 206, and a sensor grip 205.

In the illustrated example, the pair of open-close bars 206 include a first open-close bar 206a (first coupler) and a second open-close bar 206b (second coupler). The sensor grip 205 includes a first grip portion 205a and a second grip portion 205b.

Similarly to Embodiment 1, the present embodiment will illustrate a construction for the sensor grip 205 and the open-close bars 206 in the case where a sensor 40 measuring 1 mm×1 mm and a thickness of 0.2 mm is to be embedded. However, the size of the sensor 40 and the construction of the sensor grip 205 and the open-close bars 206 are not limited to this example. Depending on the size of the sensor 40, the construction may be altered as appropriate.

Similarly to Embodiment 1, the support shaft 27 may have a cylindrical shape. The support shaft 27 is designed with a diameter that permits friction-free movement inside the needle. In the present embodiment, the diameter of the support shaft 27 is e.g. 1.65 mm.

One end of open-close bars 206 is attached to the support shaft 27, within a circular side face of the support shaft 27, for example. The length (L3) of the open-close bars 206 shown in FIG. 13 is e.g. 5 mm.

In the construction illustrated in FIG. 13, the open-close bars 206 are attached to the support shaft 27 so that their longitudinal directions are substantially parallel. Herein, the first angle (R4a), which is an angle constituted by the first open-close bar 206a and the center line B of the support shaft 27 is set to e.g. about 0 degrees this defining a first initial angle, (see FIG. 14 described later). Moreover, the second angle (R4b), which is an angle constituted by the second open-close bar 206b and the center line B of the support shaft 27, is set to e.g. about 0 degrees, this defining a second initial angle (see FIG. 14 described later). At the place where the open-close bars 206 are attached to the support shaft 27, there is an interspace (W) of e.g. about 0.8 mm between the first open-close bar 206a and the second open-close bar 206b.

In the example shown in FIG. 13, the sensor grip 205 is arranged so that each grip portion 205a or 205b constitutes an angle (R3) of about 5 degrees with the respective open-close bar 206. The values of the length L3 and the angle R3 are not limited respectively to 5 mm and 5 degrees. The length L3 and the angle R3 may have any values that permit fixing and freeing of the sensor 40, without being limited to specific values.

FIG. 14 is a schematic cross-sectional view of the sensor-retaining rod 21 and the needle 32 as being cut along a plane which is parallel to the X-Z plane, when the sensor-retaining rod 21 of the present embodiment is placed in the needle hole 31.

The needle 32 may have a thickness of e.g. 14 G. That is, it may have an inner diameter of 1.69 mm and an outer diameter of 2.11 mm.

The sensor-retaining rod 21 is placed in the needle hole 31. As a result, stress acts on the first open-close bar 206a and the second open-close bar 206b to deform the open-close bars 206. As a result of this, the first angle (R4a), which is an angle constituted by the first open-close bar 206a and the center line B of the support shaft 27, equals e.g. about −5 degrees. Moreover, the second angle (R4b), which is an angle constituted by the second open-close bar 206b and the center line B of the support shaft 27, equals e.g. about −5 degrees. Thus, the sensor 40 becomes sandwiched by the sensor grip 205, whereby the sensor 40 is fixed. In the construction illustrated in FIG. 14, when inside the needle hole 31, at least one of the first open-close bar 206a and the second open-close bar 206b is not in contact with the inner wall of the needle hole 31.

FIG. 15 is a schematic cross-sectional view of the sensor grip 205 and open-close bars 206 as being cut along a plane which is parallel to the X-Z plane, in a state where they are outside the needle hole 31 of the needle 32.

In Embodiment 4, when the sensor grip 205 and the open-close bars 206 go outside the needle hole 31, restoration from deformation occurs due to elasticity of the first open-close bar 206a and the second open-close bar 206b, whereby the open-close bars 206 become spread. For example, when the first open-close bar 206a goes outside the needle hole 31, the first angle R4a (see FIG. 14) becomes as large as the first initial angle (about 0 degrees). When the second open-close bar 206b goes outside the needle hole 31, the second angle R4b (see FIG. 14) becomes as large as the second initial angle (about 0 degrees). As a result, the sensor 40 is freed from the sensor grip 205.

In the present embodiment, the sensor grip 205 may be similar in structure to the sensor grip 25 of Embodiment 1. However, the present embodiment differs from Embodiment 1 in that the sensor grip 205 is fixed at an angle of e.g. about 5 degrees to the open-close bars 206. The shape of the sensor grip 205 is not limited to any particular shape. A shape similar to that of the sensor grip 95 in Embodiment 2 or a shape similar to that of the sensor grip 105 in Embodiment 3 may be adopted.

Other component elements and the operation when embedding the sensor 40 may be identical to those of Embodiment 1. Therefore, their description will be omitted.

As described above, in the sensor embedding device of Embodiment 4, the first coupler (first open-close bar 206a) and the second coupler (second open-close bar 206b) are provided so that, when inside the needle hole 31, they are not in contact with the inner wall of the needle hole 31 (which may also be considered as the inner wall of the needle 32). Note that the first coupler (first open-close bar 206a) and the second coupler (second open-close bar 206b) may be arranged so that at least one of them is not in contact the inner wall of the needle hole 31 when inside the needle hole 31.

Thus, according to Embodiment 4, the portion of the sensor-retaining rod 21 that may potentially come in contact with the inner wall of the needle hole 31 can be reduced. This allows for more smooth insertion of the sensor.

Embodiment 5

With reference to FIG. 16 to FIG. 19, Embodiment 5 of the present disclosure will be described. The present embodiment differs from Embodiments 1 to 4 in that the sensor grip 305 of the present embodiment fixes the sensor 40 from above and below.

Figure 16:
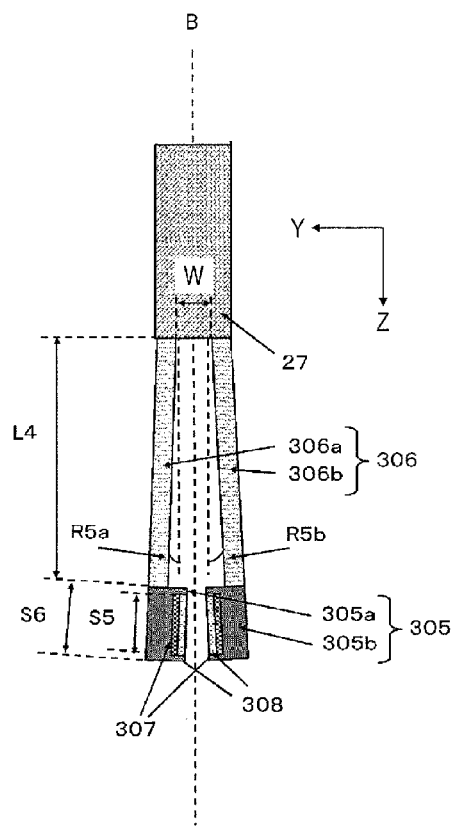
FIG. 16 is a Y-Z cross-sectional view of a sensor-retaining rod 21 according to Embodiment 5 of the present disclosure.

FIG. 16 is a schematic cross-sectional view of the sensor-retaining rod 21 of the present embodiment as being cut along a plane which is parallel to the Y-Z plane (see FIG. 1). As shown in FIG. 16, the sensor-retaining rod 21 of the present embodiment includes a support shaft 27, a pair of open-close bars 306, and a sensor grip 305.

In the illustrated example, the pair of open-close bars 306 include a first open-close bar 306a (first coupler) and a second open-close bar 306b (second coupler). The sensor grip 305 includes a first grip portion 305a and a second grip portion 305b. In the present embodiment, the sensor surface of the sensor 40, which includes a sensing region, is oriented toward the first grip portion 305a.

The present embodiment will illustrate a construction for the support shaft 27, the open-close bars 306, and the sensor grip 305 in the case where a sensor 40 measuring 1 mm×1 mm and a thickness of 0.2 mm is to be embedded. However, the size of the sensor 40 and the construction of the support shaft 27, the open-close bars 306, and the sensor grip 305 are not limited to this example. Depending on the size of the sensor 40, the construction may be altered as appropriate.

Similarly to Embodiment 1, the support shaft 27 may have a cylindrical shape. The support shaft 27 is designed with a diameter that permits friction-free movement inside the needle. In the present embodiment, the diameter of the support shaft 27 is e.g. 1.65 mm.

One end of each open-close bar 306 is attached in a circular side face of the support shaft 27, for example. At the place where the open-close bars 306 are attached to the support shaft 27, there is an interspace (W) of e.g. about 0.8 mm between the first open-close bar 306a and the second open-close bar 306b. The open-close bars 306 may be shaped similarly to those in Embodiment 1. The length (L4) of the open-close bars 306 shown in FIG. 16 is e.g. 5 mm.

Herein, the first angle (R5a), which is an angle constituted by the first open-close bar 306a and the center line B of the support shaft 27, is set to e.g. about 3 degrees, this defining a first initial angle. Moreover, the second angle (R5b), which is an angle constituted by the second open-close bar 306b and the center line B of the support shaft 27, is set to e.g. about 3 degrees, this defining a second initial angle. As shown in the figure, each of the first grip portion 305a and the second grip portion 305b has two recesses 307 and 308.

The length L4, the first initial angle, and the second initial angle may have any values that permit fixing and freeing of the sensor 40, without being limited to specific values.

Figure 17:
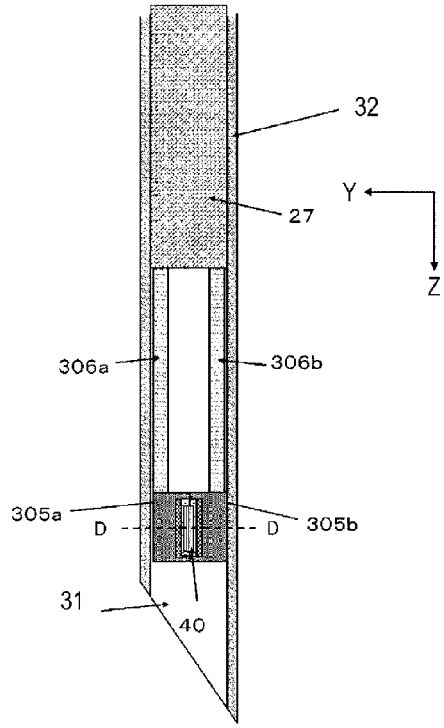
FIG. 17 is a Y-Z cross-sectional view of the sensor-retaining rod 21 and a needle 32 according to Embodiment 5 of the present disclosure when the sensor-retaining rod 21 is placed in a needle hole 31.

FIG. 17 is a schematic cross-sectional view of the sensor-retaining rod 21 of the present embodiment being placed in the needle hole 31, when the sensor-retaining rod 21 and the needle 32 are cut along a plane which is parallel to the Y-Z plane.

The needle 32 may have a thickness of e.g. 14 G. That is, it may have an inner diameter of 1.69 mm and an outer diameter of 2.11 mm.

The sensor-retaining rod 21 is placed in the needle hole 31. As a result, stress acts on the first open-close bar 306a and the second open-close bar 306b to deform the open-close bars 306. This causes the pair of open-close bars 306 to become parallel. That is, in the illustrated example, the first angle R5a (see FIG. 16) is about 0 degrees inside the needle hole 31. The second angle R5b (see FIG. 16) is about 0 degrees inside the needle hole 31. As a result, the sensor 40 is fixed by the sensor grip 305.

Figure 18:
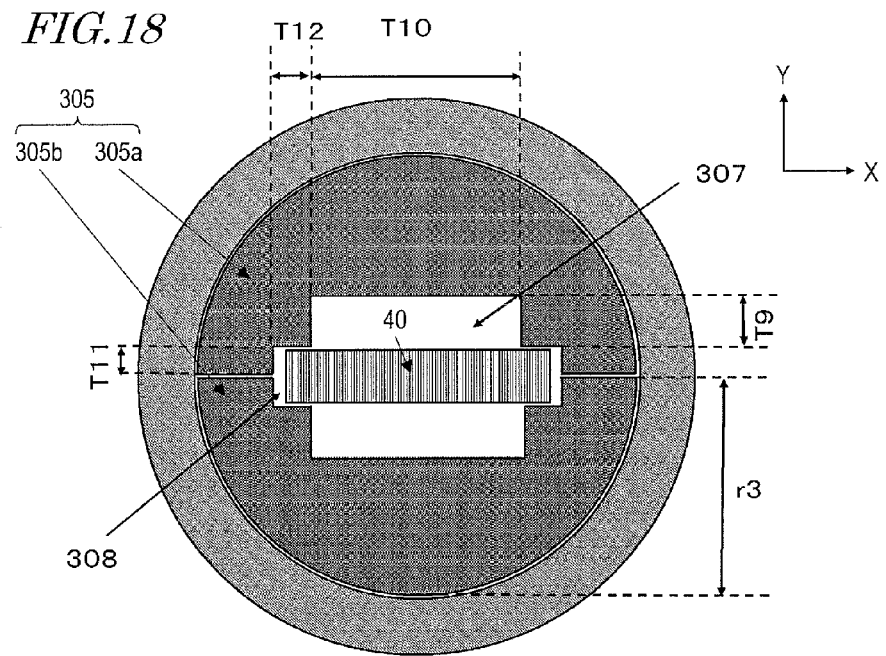
FIG. 18 is an X-Y cross-sectional view of a sensor grip 305 according to Embodiment 5 of the present disclosure.

With reference to FIG. 18, a method of fixing the sensor 40 with the sensor grip 305 will be described.

FIG. 18 is schematic cross-sectional view (a cross-sectional view taken along line D-D shown in FIG. 17) when the sensor grip 305 is cut along a plane which is parallel to the X-Y plane. In the example shown in FIG. 18, the sensor grip 305 (i.e., the first grip portion 305a and the second grip portion 305b) has a recess 307 for avoiding contact with the sensor surface and a recess 308 into which the sensor 40 is to be fitted. The recesses 307 and 308 have a width (S5) of e.g. 1.1 mm along the Z direction (see FIG. 16). The sensor grip 305 has a width (S6) of e.g. 1.5 mm along the Z direction (see FIG. 16). So long as the sensor 40 is able to be fixed, the values of the width S5 and the width S6 are not limited respectively to 1.1 mm and 1.5 mm.

In the construction illustrated in FIG. 18, the first grip portion 305a and the second grip portion 305b are each semicylindrical. In the illustrated example, the sensor grip 305 has a radius of curvature (r3) of about 0.8 mm. The recess 307 has a depth (T9) of 0.2 mm. The recess 307 has a width (T10) of 0.8 mm. The recess 308 has a depth (T11) of 0.1 mm and a width (T12) of 0.15 mm.

The open-close bars 306 may be similar in size and shape to those of Embodiment 3.

The materials of the open-close bars 306 and the sensor grip 305 are not limited to any particular materials so long as they are elastic and capable of being processed. Examples of the material of the sensor grip 305 include metals, alloys, resins, etc. Examples of processing methods for the support shaft 27, the open-close bars 306, and the sensor grip 305 include cutting processes, laser processes, etc. The processing methods are not limited to any particular methods so long as they are capable of processing these materials.

Figure 19:
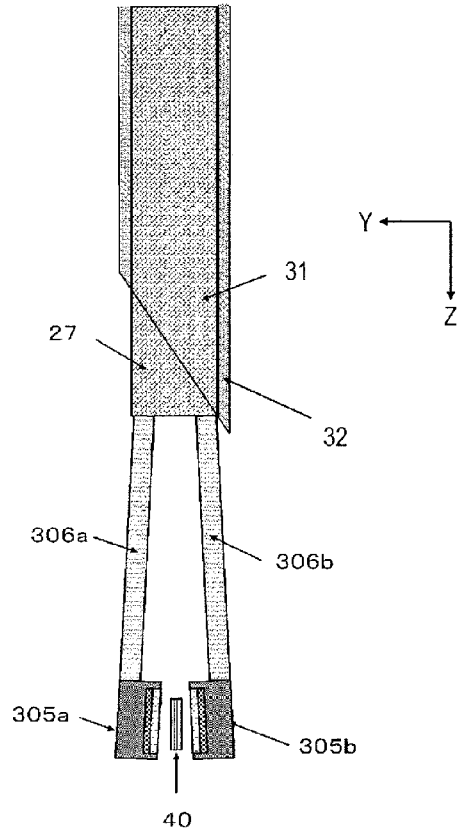
FIG. 19 is a Y-Z cross-sectional view of the sensor grip 305 and open-close bars 306 according to Embodiment 5 of the present disclosure in a state where they are outside the needle hole 31 of the needle 32.

FIG. 19 is a schematic cross-sectional view of the sensor grip 305 and open-close bars 306 as being cut along a plane which is parallel to the Y-Z plane, in a state where they are outside the needle hole 31 of the needle 32.

In Embodiment 5, when the sensor grip 305 and the open-close bars 306 go outside the needle hole 31, restoration from deformation occurs due to elasticity of the first open-close bar 306a and the second open-close bar 306b, whereby the open-close bars 306 become spread. For example, when the first open-close bar 306a goes outside the needle hole 31, the first angle R5a (see FIG. 16) becomes as large as the first initial angle (about 3 degrees). When the second open-close bar 306b goes outside the needle hole 31, the second angle R5b (see FIG. 16) becomes as large as the second initial angle (about 3 degrees). As a result, the sensor 40 is freed from the sensor grip 305.

Other component elements and the operation when embedding the sensor 40 may be identical to those of Embodiment 1. Therefore, their description will be omitted.

In the sensor embedding device of Embodiment 5, the first grip portion 305a is located on the side where the sensing region of the sensor is situated (i.e., the front face). On the other hand, the second grip portion 305b is located on the opposite side from the side where the sensing region of the sensor is situated (e.g., the rear face).

In Embodiment 5, the amounts of change that the angles of the open-close bars 306 undergo in order to free the sensor 40 are relatively small. This facilitates removal from the subject, thus reducing the damage on the subject.

Now, referring to FIG. 21, the sensor embedding device according to another illustrative embodiment of the present disclosure will be described in outline.

Figure 21:
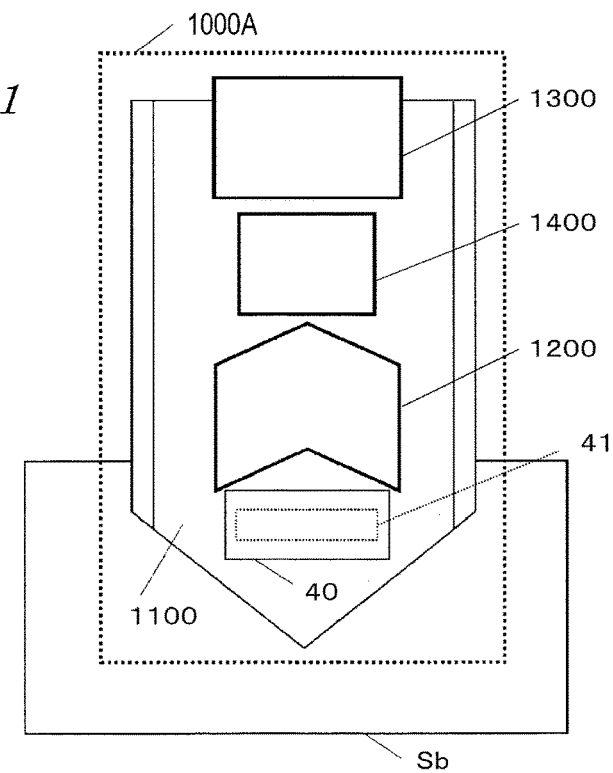
FIG. 21 is a diagram showing in outline a sensor embedding device 1000A according to another illustrative embodiment of the present disclosure.

FIG. 21 is a diagram showing in outline a sensor embedding device 1000A according to another illustrative embodiment of the present disclosure.

The sensor embedding device 1000A according to another illustrative embodiment of the present disclosure embeds a sensor 40 in a subject Sb. The sensor embedding device 1000A includes a needle 1100, a sensor retainer 1200, a movable section 1300, and a sensor retention releaser 1400. The sensor retention releaser 1400 releases the sensor 40 from retention by the sensor retainer 1200.

With this construction, too, a sensor 40 can be embedded inside a subject Sb in such a manner that its sensing region 41 is oriented in a predetermined direction. This allows the sensor to be embedded so that the sensor surface having a sensing region is oriented toward the skin surface of a biological body, for example. Since the sensor embedding device includes the sensor retention releaser, the sensor can be released from retention by the sensor retainer with higher precision.

Embodiment 6

With reference to FIG. 21 to FIG. 29, Embodiment 6 of the present disclosure will be described.

The present embodiment differs from Embodiments 1 to 5 in that the sensor embedding device includes a sensor retention releaser.

Figure 22:
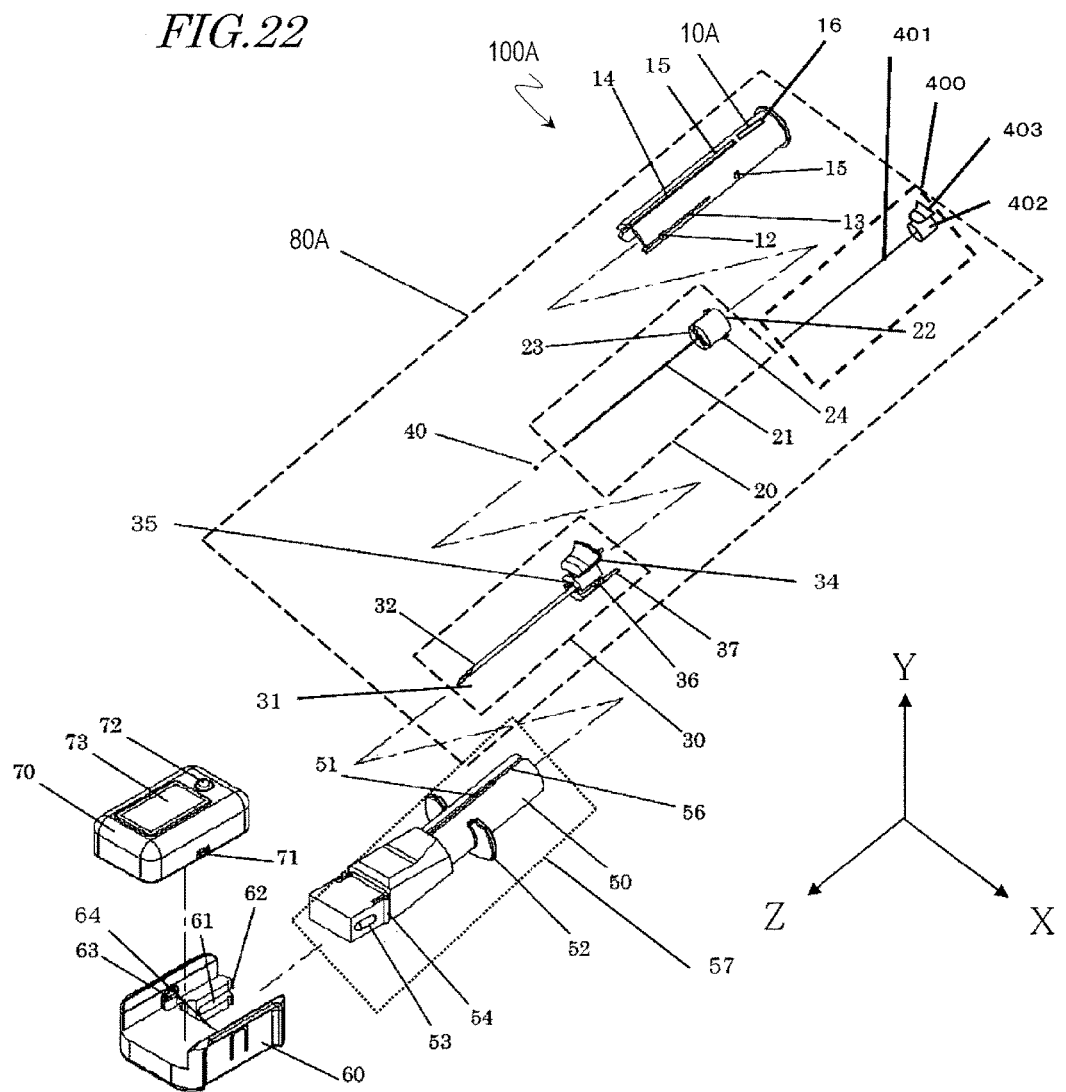
FIG. 22 is an exploded view showing an exemplary construction of a sensor embedding device 100A according to Embodiment 6 of the present disclosure.

FIG. 22 is an exploded view showing an exemplary construction of a sensor embedding device 100A according to Embodiment 6 of the present disclosure. In the construction illustrated in FIG. 22, a plunger unit 80A of the sensor embedding device 100A includes a sensor-retaining unit 20, a needle unit 30, a plunger 10, and a push bar unit 400.

The sensor-retaining unit 20 includes a sensor-retaining rod 21 and a sensor-retaining rod fixture 22. As will be described later, in the present embodiment, a support shaft 27 of the sensor-retaining rod 21 is hollow.

The plunger 10A shown in FIG. 22 includes a needle unit guide slit 14, a push bar unit guide slit 16, needle unit setting holes 12, and needle unit pullback release slits 13. Two needle unit setting holes 12 and two needle unit pullback release slits 13 are formed in the plunger 10A. In the plunger 10A, the needle unit setting holes 12 and the needle unit pullback release slits 13 are at places that are symmetric in terms of right and left.

In the construction illustrated in FIG. 22, the push bar unit 400 includes a push bar 401, a push bar retainer 402, and a push bar slide lever 403. The push bar 401 is inserted in a hollow portion of the support shaft 27.

Figure 23:
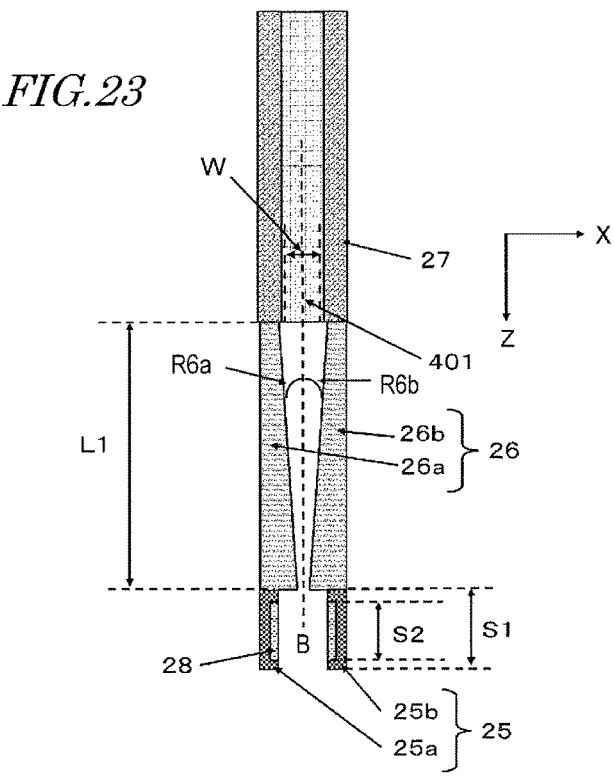
FIG. 23 is an X-Z cross-sectional view of a sensor-retaining rod 21 and a push bar 401 according to Embodiment 6 of the present disclosure.

FIG. 23 is a schematic cross-sectional view of the sensor-retaining rod 21 and the push bar 401 as being cut along a plane which is parallel to the X-Z plane (see FIG. 22).

In the construction illustrated in FIG. 23, the sensor-retaining rod 21 includes the hollow support shaft 27, a pair of open-close bars 26, and a sensor grip 25. Herein, the push bar 401 has a cylindrical shape.

The present embodiment will illustrate a construction for the support shaft 27, the open-close bars 26, the sensor grip 25, and the push bar 401 in the case where a sensor 40 measuring 1 mm×1 mm and a thickness of 0.2 mm is to be embedded. However, the size of the sensor 40 and the construction of the support shaft 27, the open-close bars 26, the sensor grip 25, and the push bar 401 are not limited to this example. Depending on the size of the sensor 40, the construction may be altered as appropriate.

The support shaft 27 may have a cylindrical shape. The support shaft 27 has a 0.8 mm hole in the center, for example. The support shaft 27 is designed with a diameter that permits friction-free movement inside the needle. In the present embodiment, the diameter of the support shaft 27 is e.g. 1.65 mm. Herein, one end of each open-close bar 26 is attached in a circular side face of the support shaft 27. The open-close bars 26 shown in FIG. 23 have a length (L1) of e.g. 5 mm. At the place where the open-close bars 26 are attached to the support shaft 27, there is an interspace (W) of e.g. about 0.8 mm between the first open-close bar 26a and the second open-close bar 26b.

The first angle (R6a), which is an angle constituted by the face of the first open-close bar 26a facing the center of the needle 32 and the center line B of the support shaft 27, is set to e.g. about 4 degrees, this defining a first initial angle. Moreover, the second angle (R6b), which is an angle constituted by the face of the second open-close bar 26b facing the center of the needle 32 and the center line B of the support shaft 27, is set to e.g. about 4 degrees, this defining a second initial angle. The length L1, the first initial angle, and the second initial angle may have any values that permit fixing and freeing of the sensor 40, without being limited to specific values.

As mentioned above, herein, the push bar 401 has a cylindrical shape. The push bar 401 has a diameter of e.g. 0.8 mm. As shown in FIG. 23, the push bar 401 is inserted in the center hole of the support shaft 27.

Figure 24:
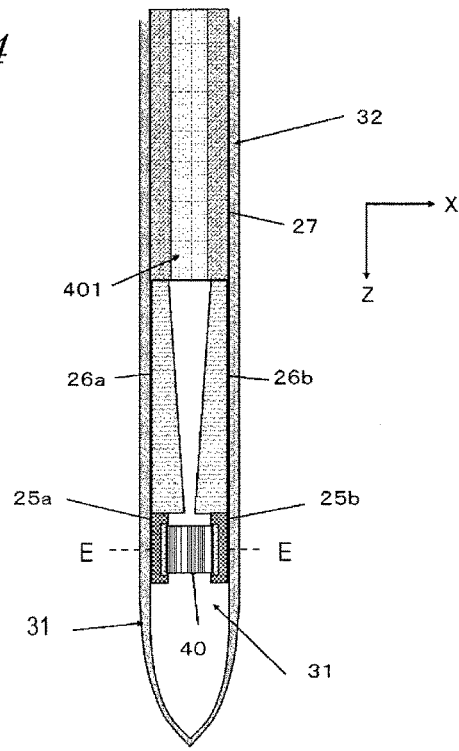
FIG. 24 is an X-Z cross-sectional view of the sensor-retaining rod 21, the needle 32, and the push bar 401 according to Embodiment 6 of the present disclosure when the sensor-retaining rod 21 and the push bar 401 are placed in a needle hole 31.

FIG. 24 is a schematic cross-sectional view of the sensor-retaining rod 21, the push bar 401, the needle 32, and the sensor 40 as being cut along a plane which is parallel to the X-Z plane, when the sensor-retaining rod 21 and the push bar 401 are placed in the needle hole 31.

As illustrated in FIG. 24, in Embodiment 6, the first grip portion 25a is located by the first side face of the sensor 40. The second grip portion 25b is located by the opposite side of the sensor 40 from the first side face.

The needle 32 may have a thickness of e.g. 14 G. That is, it may have an inner diameter of 1.69 mm and an outer diameter of 2.11 mm.

Next, with reference to FIG. 25, a method of fixing the sensor 40 with the sensor grip 25 will be described.

Figure 25:
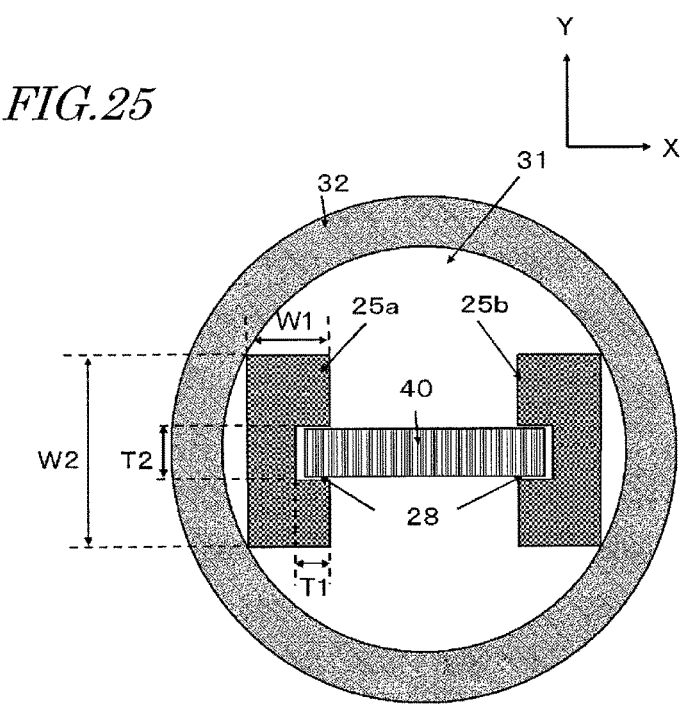
FIG. 25 is an X-Y cross-sectional view of a sensor grip 25 according to Embodiment 6 of the present disclosure.

FIG. 25 is a schematic cross-sectional view (a cross-sectional view taken along line E-E shown in FIG. 24) when the sensor grip 25 is cut along a plane which is parallel to the X-Y plane.

In the example shown in FIG. 25, the sensor grip 25 (i.e., the first grip portion 25a and the second grip portion 25b) has a recess 28 into which the sensor 40 is to be fitted.

In the illustrated example, the sensor grip 25 has a width (W1) of 0.35 mm along the X direction and a width (W2) of 0.8 mm along the Y direction. The recess 28 has a depth (T1) of 0.15 mm and a width (T2) of 0.2 mm. The width T2 is slightly larger than the sensor thickness.

The portion of the open-close bars 26 that provides fixture to the support shaft 27 may have a rectangular shape. This fixture portion has a width of e.g. 0.35 mm along the X direction, and a width of e.g. 0.8 mm along the Y direction.

The material of the push bar 401 is not limited to any particular material so long as it is capable of being processed. Examples of the material of the push bar 401 include metals, alloys, resins, etc.

The recess 28 has a width (S2) of e.g. 1.1 mm along the Z direction (see FIG. 23). The sensor grip 25 has a width (S1) of e.g. 1.5 mm along the Z direction (see FIG. 23). So long as the sensor 40 is able to be fixed, the values of the width S2 and the width S1 are not limited respectively to 1.1 mm and 1.5 mm.

Figure 26:
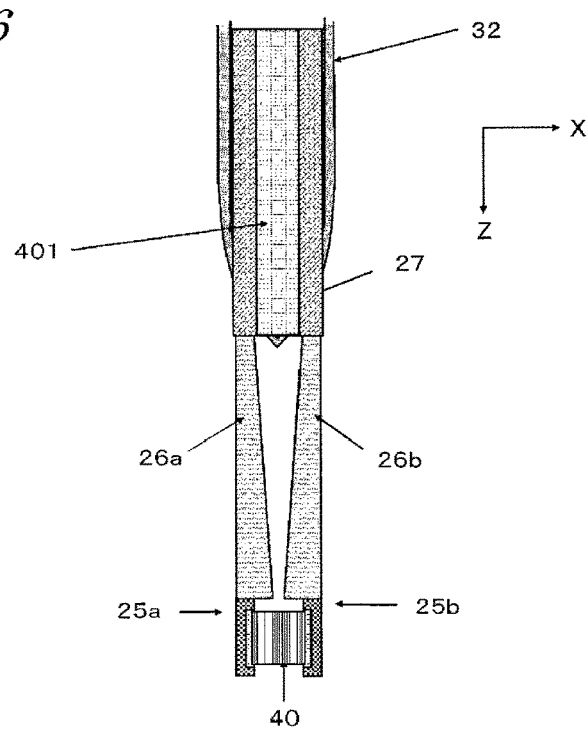
FIG. 26 is an X-Z cross-sectional view of the sensor grip 25, open-close bars 26, and push bar 401 in a state where they are outside the needle hole 31 of the needle 32.

FIG. 26 is a schematic cross-sectional view of the sensor grip 25 and the open-close bars 26 as being cut along a plane which is parallel to the X-Z plane, in a state where they are outside the needle hole 31 of the needle 32. In the present embodiment, even when the sensor grip 25 and the open-close bars 26 go outside the needle hole 31, the interspace between the open-close bars 26 (i.e., the interspace between the first open-close bar 26a and the second open-close bar 26b) is conserved, so that the sensor grip 25 keeps the sensor 40 fixed even outside the needle hole 31.

Figure 27:
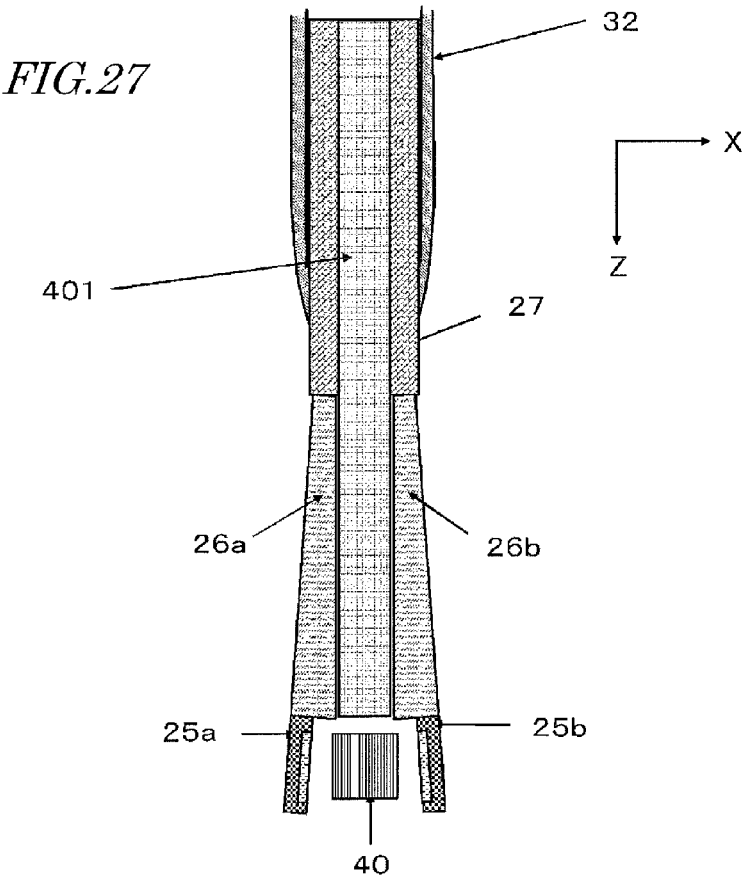
FIG. 27 is an X-Z cross-sectional view of the sensor grip 25, open-close bars 26, push bar 401, and sensor 40 in a state where the sensor grip 25 has freed the sensor 40.

FIG. 27 is a schematic cross-sectional view of the sensor grip 25 and the open-close bars 26 as being cut along a plane which is parallel to the X-Z plane, in a state where the push bar 401 is pushed out. FIG. 27 shows a state where, beginning from the state shown in FIG. 26, the push bar 401 is further pushed out toward the sensor grip 25. As shown in FIG. 27, as the push bar 401 is pushed out, the open-close bars 26 become spread, thus freeing the sensor 40.

As described above, the sensor embedding device of Embodiment 6 includes a sensor retention releaser for releasing the sensor from retention by the sensor retainer. For example, in Embodiment 6, the sensor retainer includes the first grip portion 25a and the second grip portion 25b. A sensor is retained by being sandwiched between the first grip portion 25a and the second grip portion 25b. When the sensor retention releaser expands the distance between the first grip portion 25a and the second grip portion 25b, the sensor is released from retention by the sensor retainer.

In Embodiment 6, the sensor retention releaser may include the push bar 401. Owing to the first open-close bar 26a, the first grip portion 25a is coupled with the support shaft 27, which is a portion of the movable section. The push bar 401 is located closer to the center of the needle hole than is the first open-close bar 26a. As the push bar 401 pushes back the first open-close bar 26a toward the outer periphery of the needle hole, the sensor retention releaser expands the distance between the first grip portion 25a and the second grip portion 25b. In Embodiment 6, owing to the second open-close bar 26b, the second grip portion 25b is coupled with the support shaft 27, which is a portion of the movable section. The push bar 401 is located closer to the center of the needle hole than is the second open-close bar 26b. As the push bar 401 pushes back the second open-close bar 26b toward the outer periphery of the needle hole, the sensor retention releaser expands the distance between the first grip portion 25a and the second grip portion 25b.

In Embodiment 6, the movable section includes a hollow support shaft as the support shaft 27. The support shaft 27 is inserted in the needle hole, so as to slide inside the needle hole. The push bar 401 is inserted into the support shaft 27, so as to slide inside the support shaft 27.

Figure 28:
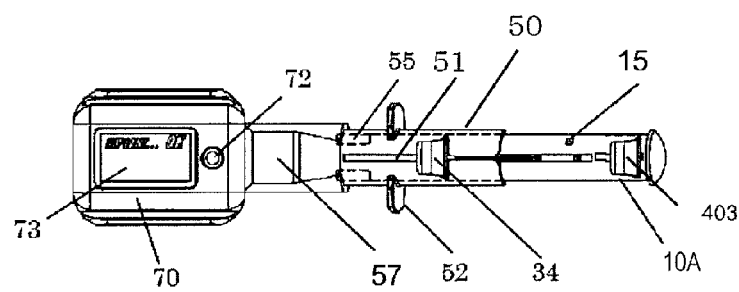
FIG. 28 is an upper plan view of the sensor embedding device 100A according to Embodiment 6 of the present disclosure.
Figure 29:
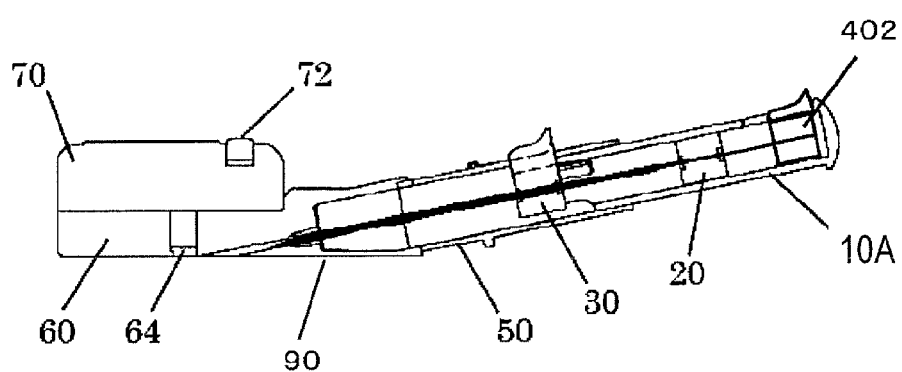
FIG. 29 is a side cross-sectional view of the sensor embedding device 100A according to Embodiment 6 of the present disclosure.
Figure 29:
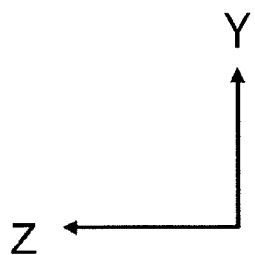

FIG. 28 is an upper plan view of the sensor embedding device 100A. FIG. 29 is a side cross-sectional view of the sensor embedding device 100A.

At use, the push bar unit 400 is set in the plunger 10A. The sensor-retaining unit 20 having the sensor-retaining rod fixture 22 with immobilizing tabs 24 provided on side faces is inserted into the plunger 10A, in such a manner that the immobilizing tabs 24 are engaged in the sensor-retaining unit setting holes 15 provided at the rear of the plunger 10A. At this time, the push bar 401 of the push bar unit 400 is inserted in the hollow portion of the support shaft 27 of the sensor-retaining unit 20.

The following can be performed in similar manners to the first embodiment: allowing the sensor 40 to be sandwiched by the sensor grip 25; insertion of the sensor-retaining rod 21 into the needle hole 31; retention of the needle unit 30 with the plunger 10A; and retention of the plunger 10A, which in itself retains the sensor-retaining unit 20 and the needle unit 30, with the cylinder unit 57. Moreover, coupling of the body unit 60 and the cylinder unit 57 and coupling of the body unit 60 and the detector 70 can also be performed in similar manners to the first embodiment. Thus, the plunger unit 80A, the cylinder unit 57, the body unit 60, and the detector 70 are coupled (see FIG. 28).

Next, with reference to the drawings, an operation when the sensor embedding device 100A of the present embodiment embeds the sensor 40 will be described.

In the embedment of the sensor 40, the operation up to pushing the sensor grip 25 and the sensor 40 out of the needle hole 31 is similar to that in the first embodiment. After the sensor grip 25 and the sensor 40 are pushed out of the needle hole 31, the finger is taken off the finger rest 52 of the cylinder unit 57, and the slide lever 34 of the needle unit 30 is pulled up. Consequently, the needle 32 exits the biological body, and the needle unit 30 abuts against the needle unit coupling surface 23 of the sensor-retaining unit 20, whereby the sensor-retaining unit 20 and the needle unit 30 become fixed.

At this point, the open-close bars 26 are still forced out of the needle hole 31. Thereafter, as the push bar slide lever 403 is slid toward the front (i.e., the positive direction on the Z axis), the push bar 401 becomes pushed out of the center hole the support shaft 27. As a result, the sensor grip 25 becomes spread, thus freeing the sensor 40.

The sensor-retaining unit release tabs 37 provided at the rear of the needle unit 30 causes the sensor-retaining unit 20 to be freed from its fixture to the plunger 10A that has been implemented by the immobilizing tabs 24. As the slide lever 34 is further pulled up, the needle unit 30, the sensor-retaining unit 20, and the push bar unit 400 are pulled up. As a result, the needle 32, the sensor-retaining rod 21, and the push bar 401 become accommodated into the cylinder 50.

Thereafter, as necessary, a confirmation button 72 on the detector 70 is pushed to check whether the sensor 40 has been properly embedded. After embedment is finished, the sensor embedding device 100A is detached from the biological body, thus completing the embedment procedure.

Embodiment 7

Embodiment 7 differs from Embodiment 6 in that the sensor grip 95 of the present embodiment has a different shape from that of the sensor grip 25 of Embodiment 6. Other than the sensor grip 95, the same construction as that of Embodiment 6 may be adopted. Therefore, common reference numerals will be given to component elements having substantially identical functions.

In the sensor embedding device of Embodiment 7, the sensor grip 95 includes a first grip portion 95a and a second grip portion 95b, similarly to the sensor embedding device of Embodiment 2 which has been described with reference to FIG. 8. Herein, the first grip portion 95a and the second grip portion 95b have semicylindrical shapes (see FIG. 8). Other component elements and the operation when embedding the sensor 40 may be identical to those of Embodiment 6. Therefore, their description will be omitted.

Note that the sensor grip 95 of the present embodiment, as cut along a plane which is parallel to the X-Y plane, has a substantially identical cross section to the cross section illustrated in FIG. 8. In other words, the cross-sectional view shown in FIG. 8 may be substantially identical to a cross-sectional view taken along line E-E shown in FIG. 24. Thus, illustration by drawings is omitted herein. The sensor embedding device of Embodiment 7 may be arranged so that at least one of the first grip portion 95a and the second grip portion 95b has a semicylindrical shape.

Thus, in this Embodiment 7, the first grip portion 95a and the second grip portion 95b are semicylindrical, similarly to Embodiment 2. This allows the number of corners of the sensor grip 95 to be decreased relative to prism shapes and the like. Thus, damage to the subject (e.g. biological tissue) during embedment can be reduced.

Embodiment 8

With reference to FIG. 30 to FIG. 33, Embodiment 8 of the present disclosure will be described. The present embodiment differs from Embodiments 6 and 7 in that the sensor grip 305 of the present embodiment fixes the sensor 40 from above and below.

Figure 30:
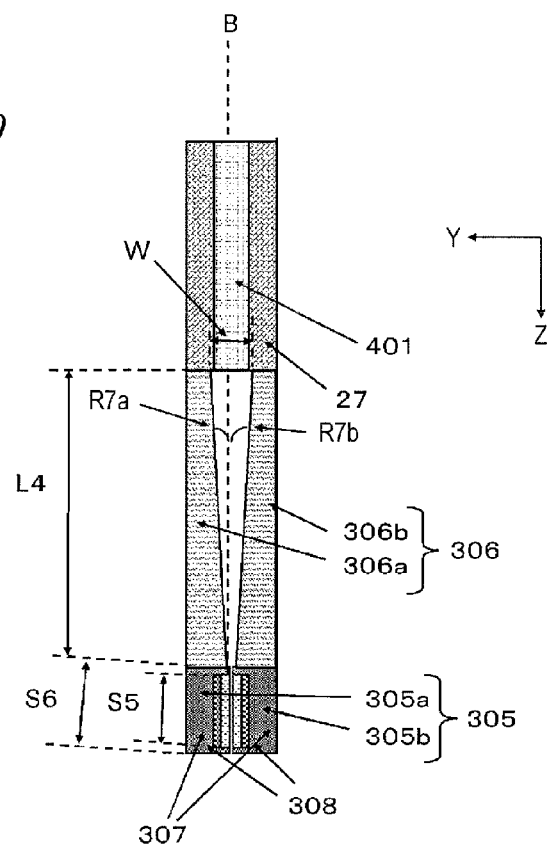
FIG. 30 is a Y-Z cross-sectional view of a sensor-retaining rod 21 and a push bar 401 according to Embodiment 8 of the present disclosure.

FIG. 30 is a schematic cross-sectional view of the sensor-retaining rod 21 and the push bar 401 of the present embodiment as being cut along a plane which is parallel to the Y-Z plane (see FIG. 22). As shown in FIG. 30, the sensor-retaining rod 21 of the present embodiment has a hollow support shaft 27, a pair of open-close bars 306, and a sensor grip 305. The sensor grip 305 includes a first grip portion 305a and a second grip portion 305b. Herein, the push bar 401 has a cylindrical shape.

In the illustrated example, the pair of open-close bars 306 includes a first open-close bar 306a (first coupler) and a second open-close bar 306b (second coupler). The length (L4) of the open-close bars 306 shown in FIG. 30 is e.g. 5 mm.

The present embodiment will illustrate a construction for the support shaft 27, the open-close bars 306, the sensor grip 305, and the push bar 401 in the case where a sensor 40 measuring 1 mm×1 mm and a thickness of 0.2 mm is to be embedded. In the present embodiment, the sensing region of the sensor 40 is oriented toward the first grip portion 305a. The size of the sensor 40 and the construction of the support shaft 27, the open-close bars 306, the sensor grip 305, and the push bar 401 are not limited to this example. Depending on the size of the sensor 40, the construction may be altered as appropriate.

For example, the support shaft 27 has a cylindrical shape. A hole having a diameter of e.g. 0.5 mm is made in the center of the support shaft 27 in this example. The support shaft 27 is designed with a diameter that permits friction-free movement inside the needle. In the present embodiment, the diameter of the support shaft 27 is e.g. 1.65 mm.

Herein, one end of each open-close bar 306 is attached in a circular side face of the support shaft 27. At the place where the open-close bars 306 are attached to the support shaft 27, there is an interspace (W) of e.g. about 0.8 mm between the first open-close bar 306a and the second open-close bar 306b.

The first angle (R7a), which is an angle constituted by the face of the first open-close bar 306a facing the center of the needle 32 and the center line B of the support shaft 27, is set to e.g. about 3 degrees, this defining a first initial angle. The second angle (R7b), which is an angle constituted by the face of the second open-close bar 306b facing the center of the needle 32 and the center line B of the support shaft 27, is set to e.g. about 3 degrees, this defining a second initial angle. The length L4, the first initial angle, and the second initial angle may have any values that permit fixing and freeing of the sensor 40, without being limited to specific values.

As mentioned above, herein, the push bar 401 has a cylindrical shape. The push bar 401 has a diameter of e.g. 0.5 mm. As shown in FIG. 30, the push bar 401 is inserted in the center hole of the support shaft 27.

Figure 31:
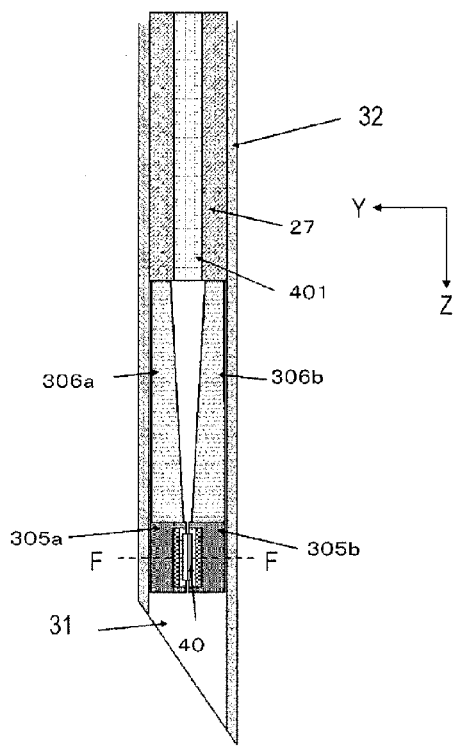
FIG. 31 is a Y-Z cross-sectional view of the sensor-retaining rod 21, needle 32, and push bar 401 according to Embodiment 8 of the present disclosure when the sensor-retaining rod 21 and the push bar 401 are placed in a needle hole 31.

FIG. 31 is a schematic cross-sectional view of the sensor-retaining rod 21, the push bar 401, the needle 32, and the sensor 40 as being cut along a plane which is parallel to the Y-Z plane, when the sensor-retaining rod 21 and the push bar 401 according to the present embodiment are placed in the needle hole 31.

The needle 32 may have a thickness of e.g. 14 G. That is, it may have an inner diameter of 1.69 mm and an outer diameter of 2.11 mm.

Next, a method of fixing the sensor 40 with the sensor grip 305 will be described. Note that the sensor grip 305 of the present embodiment, as cut along a plane which is parallel to the X-Y plane, has a substantially identical cross section to the cross section illustrated in FIG. 18. In other words, the cross-sectional view shown in FIG. 18 may be substantially identical to a cross-sectional view taken along line F-F shown in FIG. 31. Thus, illustration by drawings is omitted herein.

As shown in FIG. 18, the sensor grip 305 (i.e., the first grip portion 305a and the second grip portion 305b) has a recess 307 for avoiding contact with the sensor surface and a recess 308 into which the sensor 40 is to be fitted.

As shown in FIG. 18, the first grip portion 305a and the second grip portion 305b are each semicylindrical. In the illustrated example, the sensor grip 305 has a radius of curvature (r3) of about 0.8 mm. The recess 307 has a depth (T9) of 0.2 mm. The recess 307 has a width (T10) of 0.8 mm. The recess 308 has a depth (T11) of 0.1 mm and a width (T12) of 0.15 mm.

The recesses 307 and 308 have a width (S5) of e.g. 1.1 mm along the Z direction (see FIG. 30). The sensor grip 305 has a width (S6) of e.g. 1.5 mm along the Z direction (see FIG. 30). So long as the sensor 40 is able to be fixed, the values of the width S5 and the width S6 are not limited respectively to 1.1 mm and 1.5 mm.

The materials of the open-close bars 306 and the sensor grip 305 are not limited to any particular materials so long as they are elastic and capable of being processed. Examples of the material of the sensor grip 305 include metals, alloys, resins, etc. The open-close bars 306 may be similar in size and shape to those of Embodiment 6. Examples of processing methods for the support shaft 27, the open-close bars 306, and the sensor grip 305 include cutting processes, laser processes, etc. The processing methods are not limited to any particular methods so long as they are capable of processing these materials.

Figure 32:
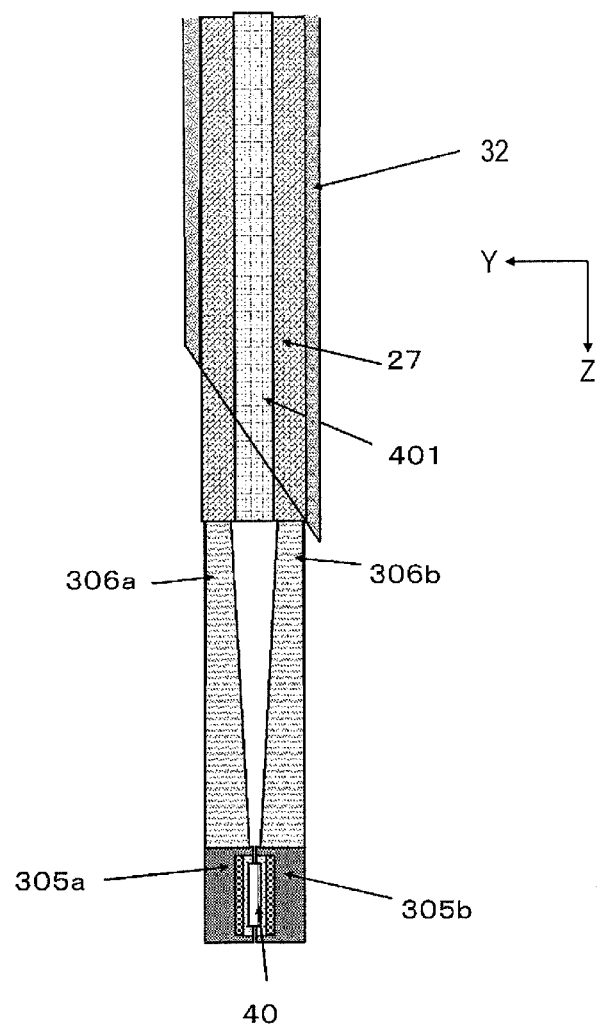
FIG. 32 is a Y-Z cross-sectional view of the sensor grip 305, open-close bars 306, and push bar 401 according to Embodiment 8 of the present disclosure in a state where they are outside the needle hole 31 of the needle 32.

FIG. 32 is a schematic cross-sectional view of the sensor grip 305 and open-close bars 306 as being cut along a plane which is parallel to the Y-Z plane, in a state where they are outside the needle hole 31 of the needle 32. In the present embodiment, even when the sensor grip 305 and the open-close bars 306 go outside the needle hole 31, the interspace between the open-close bars 306 (i.e., the interspace between the first open-close bar 306a and the second open-close bar 306b) is conserved, so that the sensor grip 305 keeps the sensor 40 fixed even outside the needle hole 31.

Figure 33:
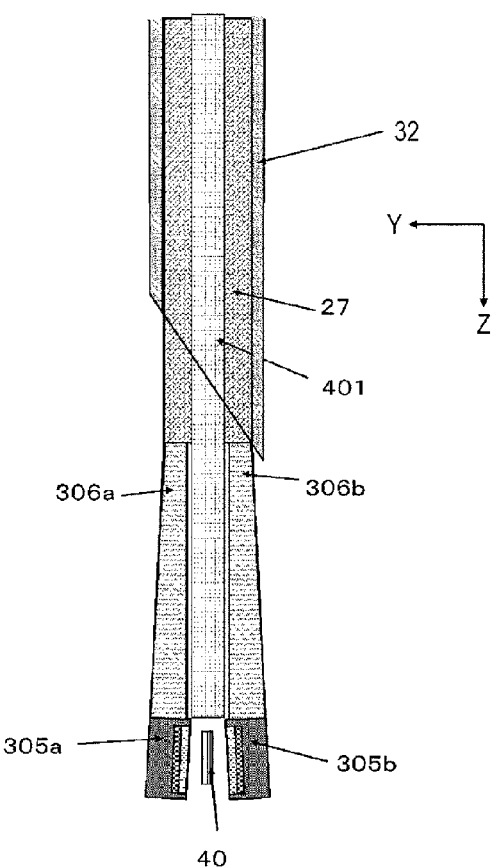
FIG. 33 is a Y-Z cross-sectional view of the sensor grip 305, open-close bars 306, push bar 401, and sensor 40 in a state where the sensor grip 305 has freed the sensor 40.

FIG. 33 is a schematic cross-sectional view of the sensor grip 305 and open-close bars 306 as being cut along a plane which is parallel to the Y-Z plane, in a state where the push bar 401 is pushed out. FIG. 33 shows a state where, beginning from the state shown in FIG. 32, the push bar 401 is further pushed out toward the sensor grip 305. As shown in FIG. 33, as the push bar 401 is pushed out, the open-close bars 306 become spread, thus freeing the sensor 40. Other component elements and the operation when embedding the sensor 40 may be identical to those of Embodiment 6. Therefore, their description will be omitted.

In the sensor embedding device of Embodiment 8, the first grip portion 305a is located on the side where the sensing region of the sensor is situated (i.e., the front face). On the other hand, the second grip portion 305b is located on the opposite side from the side where the sensing region of the sensor is situated (e.g., the rear face).

In Embodiment 8, the amounts of change that the angles of the open-close bars 306 undergo in order to free the sensor 40 are relatively small. This facilitates removal from the subject, thus reducing the damage on the subject.

Next, with reference to FIG. 34, still another illustrative embodiment of the present disclosure will be described.

Figure 34:
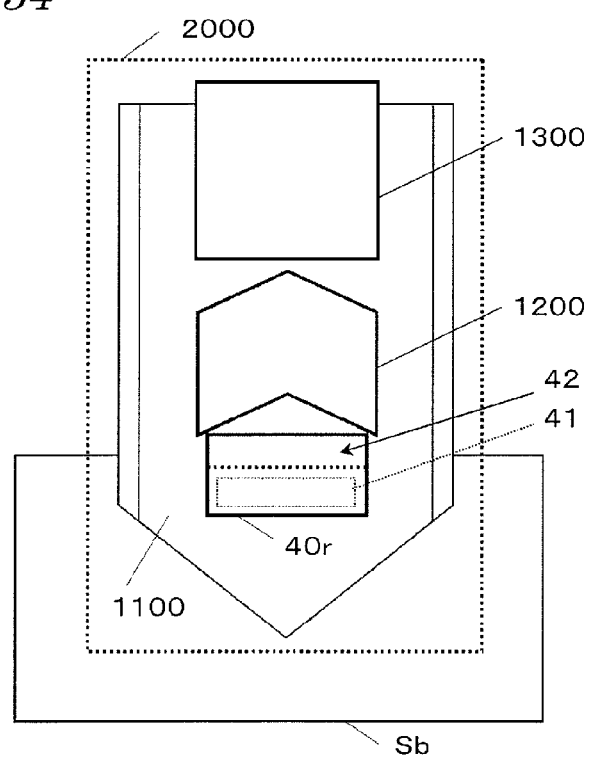
FIG. 34 is a diagram showing in outline a sensor embedding system 2000 according to still another illustrative embodiment of the present disclosure.

FIG. 34 is a diagram showing in outline a sensor embedding system 2000 according to still another illustrative embodiment of the present disclosure. The sensor embedding system 2000 according to still another illustrative embodiment of the present disclosure embeds a sensor in a subject.

In the construction illustrated in FIG. 34, the sensor embedding system 2000 includes a sensor 40r and a sensor embedding device. The sensor 40r has a sensing region 41 for detecting the state of a subject Sb and a retained portion 42.

In the construction illustrated in FIG. 34, the sensor embedding device includes a needle 1100, a sensor retainer 1200, and a movable section 1300. As the sensor embedding device, the above-described sensor embedding device 1000 or the sensor embedding device 1000A can be used, for example. The sensor embedding device may be any of the sensor embedding devices of Embodiments 1 to 8, for example.

The sensor retainer 1200 may include a first grip portion and a second grip portion. In the present embodiment, a sensor 40r becomes retained as the retained portion 42 is sandwiched between the first grip portion and the second grip portion.

With this construction, too, a sensor can be embedded inside a subject in such a manner that its sensing region is oriented in a predetermined direction. This allows the sensor to be embedded so that the sensor surface having a sensing region is oriented toward the skin surface of a biological body, for example. Since the sensor has a retained portion, the retained portion being sandwiched between the first grip portion and the second grip portion, the sensor retainer can retain the sensor with higher precision.

Hereinafter, other examples of the sensor embedding system and the sensor will be described.

Embodiment 9

With reference to FIG. 34 to FIG. 39, Embodiment 9 of the present disclosure will be described. As the subject, the present embodiment illustrates a biological body (e.g., a human or animal body). In the present embodiment, the sensor is exemplified by a sensor chip 40c. The present embodiment will illustrate the structure of the sensor chip 40c, and a sensor embedding system including a sensor embedding device which embeds the sensor chip 40c, in the case where surface-enhanced Raman scattering spectroscopy is adopted as the optical technique.

The needle 32 according to the present embodiment has a needle hole 31 through which the sensor chip 40c and the sensor-retaining rod 21 are to move inside.

Figure 35:
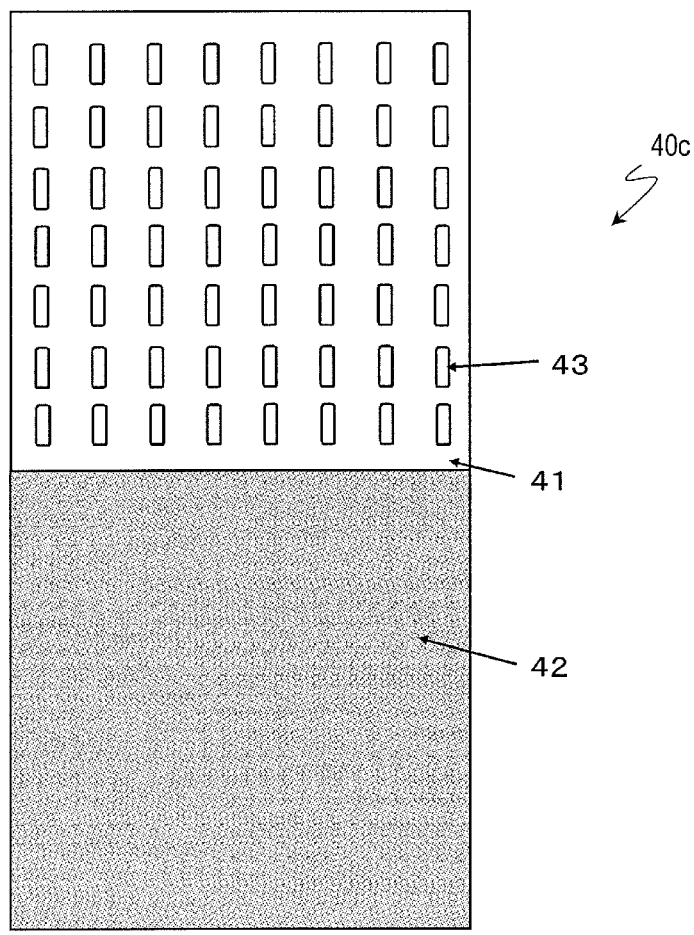
FIG. 35 is a schematic upper plan view of a sensor chip 40c according to Embodiment 9 of the present disclosure.

FIG. 35 is a schematic upper plan view showing an illustrative construction of the sensor chip 40c. The sensor chip 40c may be sized as follows, for example.

thickness: t=0.2 mm
width: w=1 mm
length: l=2 mm

In the construction illustrated in FIG. 35, the sensor chip 40c has a sensing region 41 measuring 1 mm×1 mm on its upper face. Moreover, the sensor chip 40c has a retained portion 42 measuring 1 mm×1 mm.

In the sensing region 41, metal nanostructures for causing surface-enhanced Raman scattering based on localized surface plasmon resonance may be formed. For example, as is schematically shown in FIG. 35, metal nanorods 43 (minor axis size: on the order of several nm to 100 nm; major axis size: about 50 to about 500 nm) whose major axes are aligned in the same direction may be used as the metal nanostructures.

For example, gold nanorods may exhibit two localized surface plasmon resonance bands. That is, localized surface plasmon resonance bands may be exhibited near 520 nm, which is associated with the minor axis directions of the rods, and at 600 to 1500 nm, which is associated with the longitudinal directions. By radiating and detecting light having a wavelength near the localized surface plasmon resonance bands, it becomes possible to take surface-enhanced Raman scattering spectroscopy measurements of an object of analysis within a biological body.

In the present embodiment, a localized surface plasmon resonance frequency exists at e.g. 700 to 1000 nm. For example, gold nanorods having an average minor axis length of 10 nm and an average major axis length of 37 nm can be used.

In the present embodiment, metal nanorods can be used as metal nanostructures. However, so long as a localized surface plasmon resonance frequency of 700 to 1000 nm is obtained, the metal nanostructures are not limited to metal nanorods. For example, metal nanodisks, metal microparticles of spherical shape, metal lines, dielectric microparticles of stacked metal layers, etc., can be used.

As the method for producing the metal nanostructures, any known technique can be used without particular limitation. For example, a pattern of microstructures may be drawn on a resist by using X-ray lithography, electron-beam lithography, or the like, then followed by metal sputtering to produce the microstructures. A die may be produced on an Si substrate by using X-ray lithography, electron-beam lithography, or the like, and nanostructures may be produced on resin by using a nanoimprinting technique, then followed by metal sputtering to produce the metal nanostructures. Alternatively, metal nanostructures which have been produced by known techniques, e.g., a synthesis method utilizing chemical reactions or a synthesis method utilizing photoreaction, may be immobilized to a substrate. It would be advantageous for the metal nanostructures to contain at least one selected from the group consisting of silver, gold, copper, aluminum, and platinum.

The retained portion 42 may be a planar surface. In the present embodiment, the sensor has a plate shape. In this case, the sensing region 41 may be a region which is formed in a portion of a principal face of the sensor chip 40c. The retained portion 42 may be a portion of the sensor chip 40c where the sensing region 41 is not formed.

Figure 36:
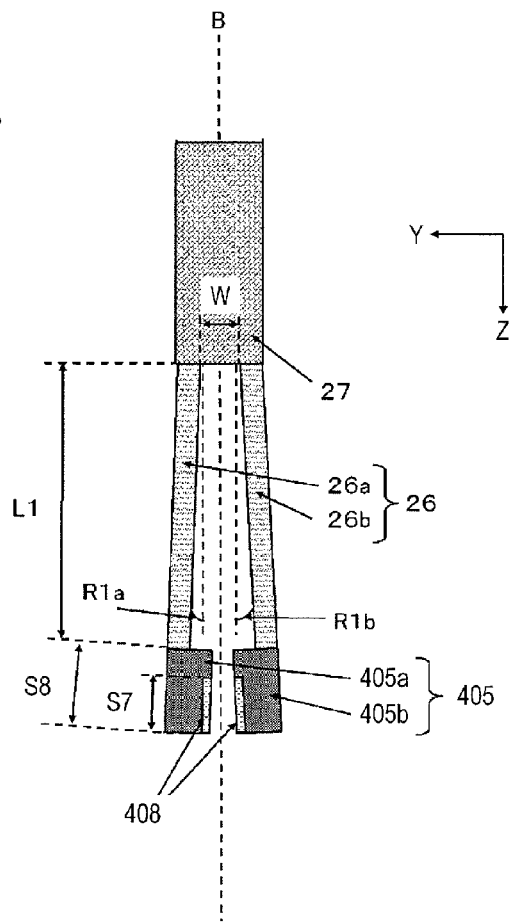
FIG. 36 is a Y-Z cross-sectional view of a sensor-retaining rod 21 according to Embodiment 9 of the present disclosure.

FIG. 36 is a schematic cross-sectional view of the sensor-retaining rod 21 of the present embodiment as being cut along a plane which is parallel to the Y-Z plane (see FIG. 1). In the construction illustrated in FIG. 36, the sensor-retaining rod 21 includes a support shaft 27, a pair of open-close bars 26, and a sensor grip 405. In the present embodiment, the sensor grip 405 fixes the sensor chip 40c from above and below. The shapes of the support shaft 27 and the pair of open-close bars 26 in the present embodiment may be substantially identical to the shapes of the support shaft and the pair of open-close bars 26 in Embodiment 1. Therefore, description of the support shaft 27 and the pair of open-close bars 26 will be omitted below.

In Embodiment 9, the sensor retainer includes a pair of open-close bars 26 and a sensor grip 405. As shown in the figure, the sensor grip 405 includes a first grip portion 405a and a second grip portion 405b. In Embodiment 9, the sensor retainer retains the sensor by sandwiching the sensor in between the first grip portion and the second grip portion.

Figure 37:
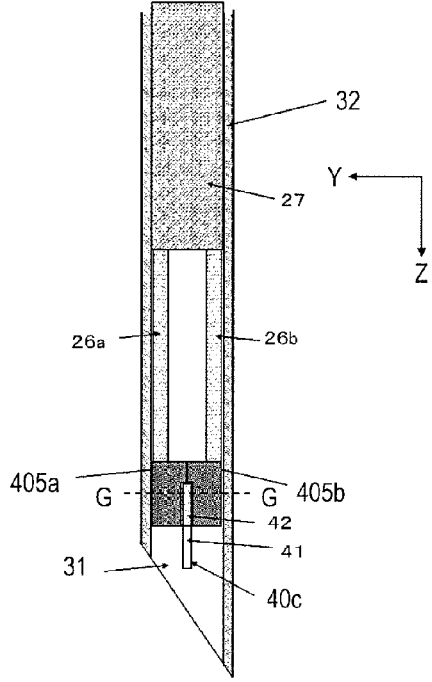
FIG. 37 is a Y-Z cross-sectional view of the sensor chip 40c, sensor-retaining rod 21, and needle 32 according to Embodiment 9 of the present disclosure when the sensor-retaining rod 21 is placed in a needle hole 31.

FIG. 37 is a schematic cross-sectional view of the sensor chip 40c, the sensor-retaining rod 21, and the needle 32 as being cut along a plane which is parallel to the Y-Z plane, when the sensor-retaining rod 21 of the present embodiment is placed in the needle hole 31.

In the sensor embedding system of Embodiment 9, the first grip portion 405a is located on the side where the sensing region of the sensor is situated (i.e., the front face). On the other hand, the second grip portion 405b is located on the opposite side from the side where the sensing region of the sensor is situated (e.g., the rear face). As shown in FIG. 37, in Embodiment 9, the sensor chip 40c becomes fixed as the sensor grip 405 sandwiches the retained portion 42.

Next, with reference to FIG. 38, a method of fixing the sensor chip 40c with the sensor grip 405 will be described.

Figure 38:
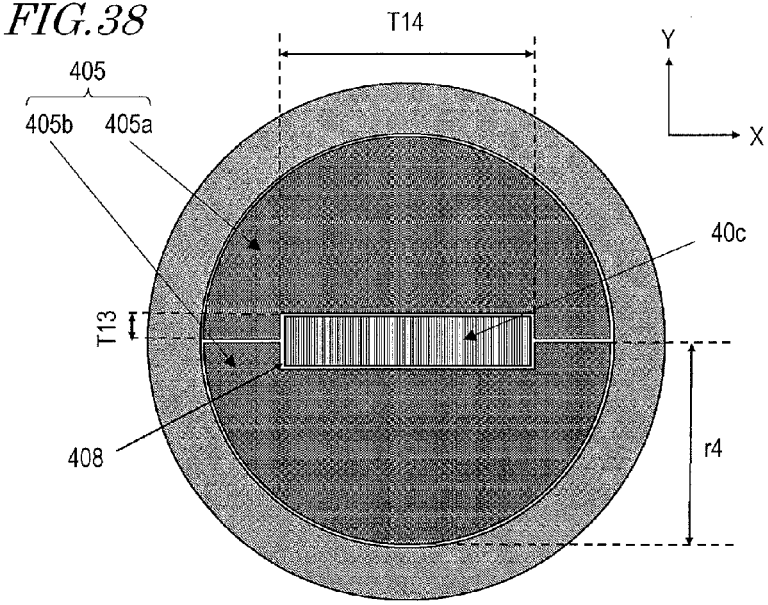
FIG. 38 is an X-Y cross-sectional view of a sensor grip 405 according to Embodiment 9 of the present disclosure.

FIG. 38 is a schematic cross-sectional view (a cross-sectional view taken along line G-G shown in FIG. 37) when the sensor grip 405 is cut along a plane which is parallel to the X-Y plane.

In the example shown in FIG. 38, the sensor grip 405 (the first grip portion 405a and the second grip portion 405b) has a recess 408 into which the sensor chip 40c is to be fitted. In the construction illustrated in FIG. 38, the first grip portion 405a and the second grip portion 405b each have a semicylindrical shape. In the construction illustrated in FIG. 38, the sensor grip 405 has a radius of curvature (r4) of 0.8 mm. The recess 408 has a depth (T13) of about 0.1 mm. The recess 408 has a width (T14) of about 1 mm. The depth T13 and the width T14 have plus tolerance with respect to 0.1 mm and 1 mm, respectively.

The recess 408 has a width (S7) of e.g. 1.1 mm along the Z direction (see FIG. 36). The sensor grip 405 has a width (S8) of e.g. 1.5 mm along the Z direction (see FIG. 36). So long as the sensor chip 40c is able to be fixed, the values of the width S7 and the width S8 are not limited respectively to 1.1 mm and 1.5 mm.

Thus, in Embodiment 9, the recess 408 is formed in the first grip portion 405a and the second grip portion 405b. The sensor is retained as the retained portion of the sensor becomes sandwiched in the recess 408 of the first grip portion 405a and in the recess 408 of the second grip portion 405b.

In this Embodiment 9, the first grip portion 405a and the second grip portion 405b are semicylindrical, as is the case with Embodiments 2 and 7. This allows the number of corners of the sensor grip 405 to be decreased relative to prism shapes and the like. Thus, damage to the subject (e.g. biological tissue) during embedment can be reduced.

The materials of the open-close bars 26 and the sensor grip 405 are not limited to any particular materials so long as they are elastic and capable of being processed. Examples of the materials of the open-close bars 26 and the sensor grip 405 include metals, alloys, resins, etc. Examples of processing methods for the support shaft 27, the open-close bars 26, and the sensor grip 405 include cutting processes, laser processes, etc. The processing methods are not limited to any particular methods so long as they are capable of processing these materials.

Figure 39:
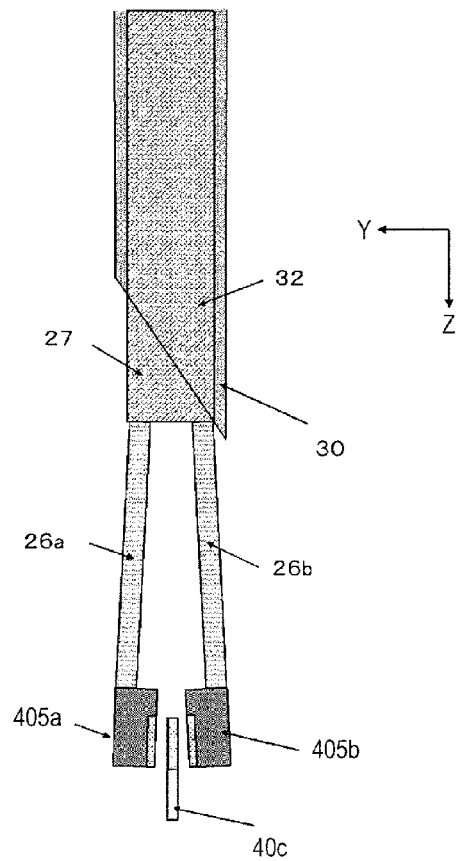
FIG. 39 is a Y-Z cross-sectional view of the sensor grip 405 and open-close bars 26 according to Embodiment 9 of the present disclosure in a state where they are outside the needle hole 31 of the needle 32.

FIG. 39 is a schematic cross-sectional view of the sensor grip 405 and the open-close bars 26 as being cut along a plane which is parallel to the Y-Z plane, in a state where they are outside the needle hole 31 of the needle 32.

In Embodiment 9, when the sensor grip 405 and the open-close bars 26 go outside the needle hole 31, restoration from deformation occurs due to elasticity of the first open-close bar 26a and the second open-close bar 26b, whereby the open-close bars 26 become spread. For example, when the first open-close bars 26a go outside the needle hole 31, the first angle R1a (see FIG. 36) becomes as large as the first initial angle (about 4 degrees). When the second open-close bar 26 goes outside the needle hole 31, the second angle R1b (see FIG. 36) becomes as large as the second initial angle (about 4 degrees).

As a result, the sensor chip 40c is freed from the sensor grip 405. Thus, in the present embodiment, the sensor is released from retention when the sensor retainer goes outside the hole of the needle, similarly to Embodiment 1. The operation when the sensor embedding device embeds the sensor chip 40c may be similar to the operation when the sensor embedding device 100 of Embodiment 1 embeds the sensor 40, as has been described with reference to FIG. 6 and FIG. 7. Therefore, the operation when the sensor embedding device embeds the sensor chip 40c will be omitted.

Similarly to the sensor embedding device according to Embodiment 1, the sensor embedding system may include a plunger, a needle guide, a cylinder into which the plunger is to be inserted, a contact portion, a pulled-out needle fixture, a pulled-out sensor retainer fixture, and a checker. The plunger retains a needle, a movable section, and a sensor retainer. The needle guide retains the needle, the movable section, and the sensor retainer, especially in a state where the needle, the movable section, and the sensor retainer have been moved to a predetermined position with a slide of the plunger. The contact portion, which comes in contact with the surface of a subject, is attached to the cylinder at a predetermined angle, the contact portion having a hole through which the needle is allowed to pass. The pulled-out needle fixture causes the needle having been pulled out from inside the subject to be fixed in the plunger. The pulled-out sensor retainer fixture causes the movable section and sensor retainer having been pulled out from inside the subject to be fixed in the plunger. The checker informs the user of a success or failure of embedment. The sensor embedding system may include an attachment with which to attach the contact portion onto the surface of the subject.

In the sensor embedding system of the above-described example, the first grip portion 405a and the second grip portion 405b have semicylindrical shapes. The sensor embedding system of Embodiment 9 may be arranged so that at least one of the first grip portion 405a and the second grip portion 405b has a semicylindrical shape. The above construction allows the number of corners of the sensor grip 405 to be decreased relative to prism shapes and the like. Thus, damage to the subject (e.g. biological tissue) during embedment can be reduced.

Moreover, in the sensor embedding system, the first grip portion 405a and the second grip portion 405b may be in contact with each other when retaining the sensor. This construction allows the sensor chip 40c to be fixed in a more stable manner.

In the case where metal nanostructures are used in the sensing region 41, not only surface-enhanced Raman scattering spectroscopy, but also surface-enhanced fluorescence spectroscopy, localized surface plasmon resonance frequency shift, change in reflectance spectrum, and the like may also be utilized as the optical technique.

The construction of the sensing region 41 is not limited to any particular construction. Instead of the metal nanostructures, fluorescent substance, absorption substance, or reflecting substance may be applied or immobilized in order to employ fluorescence spectroscopy, absorption spectroscopy, reflectance spectroscopy, or the like.

In Embodiments 1 to 9, in the case where returned light or the like from the sensor (e.g., Raman-scattered light or fluorescence) is to be detected at the opposite side of the side where the needle is to be inserted, for example, the sensor may be embedded in such a manner that its sensing region is oriented toward the opposite side of the side where the needle is to be inserted. Thus, the sensor embedding device may embed the sensor in such a manner that its sensing region is oriented toward the side where returned light or the like from the sensor (e.g., Raman-scattered light or fluorescence) is to be detected. Similarly, the sensor embedding system may embed the sensor in such a manner that its sensing region is oriented toward the side where returned light or the like from the sensor (e.g., Raman-scattered light or fluorescence) is to be detected.

In Embodiments 1 to 5 and 9, only one of the first coupler and the second coupler may undergo deformation and restoration so as to change the distance between the first grip portion and the second grip portion. In other words, when the first and second couplers goes outside the hole, it may be only one of the first angle and the second angle that is increased.

In Embodiments 6 to 8, only one of the first open-close bar (first coupler) and the second open-close bar (second coupler) may be pushed aside by the push bar so as to change the distance between the first grip portion and the second grip portion. In other words, the construction may be arranged so that only one of the first open-close bar (first coupler) and the second open-close bar (second coupler) is pushed aside by the push bar.

In Embodiments 1 to 9, the subject may be a human or animal body. Alternatively, the subject may be inanimate.

In Embodiments 1 to 9, as the subject state, presence or absence of an analyte within the subject, etc., may be detected by using a sensor. As the subject state, concentration of an analyte within the subject may be measured by using a sensor. In this case, the analyte may be glucose, lactic acid, pyruvic acid, acetoacetic acid, 3-hydroxy butyric acid (β-hydroxy butyric acid), or the like, for example.

The shape of the sensor is not limited only to a chip shape (plate shape). The sensor shape may be any shape that permits retention by the sensor retainer. The sensor may have a shape that is complete with a retained portion.

Any of the constructions shown in Embodiments 1 to 9 may be combined as appropriate.

A sensor embedding device and sensor embedding system according to the present disclosure may be useful in, for example, an apparatus which transdermally measures or monitors an analyte (object of analysis) within a biological body by using an optical technique.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A sensor embedding device for embedding a sensor in a subject, the sensor having a sensing region in which to detect a state of the subject, comprising:
a needle to be inserted in the subject, the needle having a hole;
a sensor retainer to retain the sensor so that the sensor is ready to be embedded inside the subject in such a manner that the sensing region is oriented in a predetermined direction;
a movable section to move the sensor into the subject with a slide of the sensor retainer inside the hole;
a plunger to retain the needle, the movable section, and the sensor retainer;
a cylinder into which the plunger is to be inserted;
a contact portion attached at a predetermined angle to the cylinder, the contact portion having a hole through which the needle passes, and the contact portion coming in contact with a surface of the subject;
a first fixture to cause the needle having been pulled out from inside the subject to be fixed in the plunger;
a second fixture to cause the movable section and sensor retainer having been pulled out from inside the subject to be fixed in the plunger; and
a checker to inform the user of a success or failure of embedment.

2. The sensor embedding device of claim 1, wherein,
the sensor retainer includes a first grip portion and a second grip portion; and
the sensor becomes retained as the sensor is sandwiched between the first grip portion and the second grip portion.

3. The sensor embedding device of claim 1, wherein the sensor is released from retention when the sensor retainer goes outside the hole.

4. The sensor embedding device of claim 2, wherein,
the distance between the first grip portion and the second grip portion is,
inside the hole, a distance which keeps the sensor retained, and
outside the hole, a distance which allows the sensor to be released from retention, the latter distance being greater than the distance between the first grip portion and the second grip portion when being inside the hole.

5. The sensor embedding device of claim 4, wherein,
the first grip portion is coupled by a first coupler with the movable section; and
given a first angle being defined as an angle constituted by the first coupler and a sliding direction of the movable section,
when the first coupler goes outside the hole, the distance between the first grip portion and the second grip portion is expanded as the first angle increases.

6. The sensor embedding device of claim 5, wherein,
the first coupler is a first open-close bar which is elastic;
the first open-close bar is attached to the movable section so that the first angle equals a predetermined first initial angle when outside the hole; and
inside the hole, the first open-close bar deforms so that the first angle becomes smaller than the first initial angle, and
when the first open-close bar goes outside the hole, the first open-close bar is restored from deformation so that the first angle becomes as large as the first initial angle.

7. The sensor embedding device of claim 5, wherein,
the second grip portion is coupled by a second coupler with the movable section; and
given a second angle being defined as an angle constituted by the second coupler and the sliding direction of the movable section,
when the second coupler goes outside the hole, the distance between the first grip portion and the second grip portion is expanded as the second angle increases.

8. The sensor embedding device of claim 7, wherein,
the second coupler is a second open-close bar which is elastic;
the second open-close bar is attached to the movable section so that the second angle equals a predetermined second initial angle when outside the hole; and
inside the hole, the second open-close bar deforms so that the second angle becomes smaller than the second initial angle, and
when the second open-close bar goes outside the hole, the second open-close bar is restored from deformation so that the second angle becomes as large as the second initial angle.

9. The sensor embedding device of claim 7, wherein at least one of the first coupler and the second coupler is not in contact with an inner wall of the hole when inside the hole.

10. The sensor embedding device of claim 2, further comprising a sensor retention releaser to release the sensor from retention by the sensor retainer, wherein
the sensor retention releaser expands the distance between the first grip portion and the second grip portion to release the sensor from retention by the sensor retainer.

11. The sensor embedding device of claim 10, wherein
the sensor retention releaser comprises a push bar;
the first grip portion is coupled by a first open-close bar with the movable section;
the push bar is located closer to the center of the hole than is the first open-close bar; and
the sensor retention releaser expands the distance between the first grip portion and the second grip portion as the push bar pushes back the first open-close bar toward an outer periphery of the hole.

12. The sensor embedding device of claim 11, wherein
the second grip portion is coupled by a second open-close bar with the movable section;
the push bar is located closer to the center of the hole than the second open-close bar; and
the sensor retention releaser expands the distance between the first grip portion and the second grip portion as the push bar pushes back the second open-close bar toward the outer periphery of the hole.

13. The sensor embedding device of claim 11, wherein,
the movable section includes a support shaft which is hollow;
the support shaft is inserted in the hole so as to slide inside the hole; and
the push bar is inserted into the support shaft so as to slide inside the support shaft.

14. The sensor embedding device of claim 2, wherein,
the first grip portion is located by a first side face of the sensor; and
the second grip portion is located by an opposite side of the sensor from the first side face.

15. The sensor embedding device of claim 2, wherein,
the first grip portion is located on a side where the sensing region of the sensor is situated; and
the second grip portion is located on an opposite side from the side where the sensing region of the sensor is situated.

16. The sensor embedding device of claim 2, wherein at least one of the first grip portion and the second grip portion has a semicylindrical shape.

17. The sensor embedding device of claim 2, wherein the first grip portion and the second grip portion are in contact with each other when retaining the sensor.

18. The sensor embedding device of claim 1, wherein the contact portion comprises an attachment with which to attach the contact portion to the surface of the subject.

19. A sensor embedding system for embedding a sensor in a subject, comprising:
the sensor,
the sensor embedding device of claim 2, wherein,
the sensor includes a sensing region in which to detect a state of the subject and a retained portion; and
the sensor becomes retained as the retained portion is sandwiched between the first grip portion and the second grip portion.

20. The sensor embedding system of claim 19, wherein,
the needle is inserted via a surface of the subject; and
the sensing region is oriented toward the surface of the subject once the sensor is embedded inside the subject.

21. The sensor embedding system of claim 19, wherein
the sensor is used to measure or monitor an analyte within a biological body by using an optical technique,
the optical technique being surface-enhanced Raman scattering spectroscopy or surface-enhanced fluorescence spectroscopy.

22. The sensor embedding system of claim 19, wherein,
a recess is formed in the first grip portion and the second grip portion; and
the sensor becomes retained as the retained portion of the sensor becomes sandwiched in the recess of the first grip portion and in the recess of the second grip portion.

23. The sensor embedding system of claim 19, wherein,
the sensor is a sensor chip having a plate shape;
the sensing region is formed in a portion of a principal face of the sensor chip; and
the retained portion is a portion of the sensor chip where the sensing region is not formed.

24. A sensor embedding device for embedding a sensor in a subject, the sensor having a sensing region in which to detect a state of the subject, comprising:
a needle to be inserted in the subject, the needle having a hole;
a sensor retainer to retain the sensor so that the sensor is ready to be embedded inside the subject in such a manner that the sensing region is oriented in a predetermined direction;
a movable section to move the sensor into the subject with a slide of the sensor retainer inside the hole;
a plunger to retain the needle, the movable section, and the sensor retainer;
a cylinder into which the plunger is to be inserted; and
a contact portion attached at a predetermined angle to the cylinder, the contact portion having a hole through which the needle passes, and the contact portion coming in contact with a surface of the subject.

* * * * *